United States Patent
Kim et al.

(10) Patent No.: US 11,512,100 B2
(45) Date of Patent: Nov. 29, 2022

(54) PREPARATION METHOD FOR EPOXY COMPOUND HAVING ALKOXYSILYL GROUP

(71) Applicant: KOREA INSTITUTE OF INDUSTRIAL TECHNOLOGY, Cheonan-si (KR)

(72) Inventors: Yun Ju Kim, Ansan-si (KR); Hyun Aee Chun, Suwon-si (KR); Su Jin Park, Osan-si (KR); Sook Yeon Park, Gunpo-si (KR)

(73) Assignee: KOREA INSTITUTE OF INDUSTRIAL TECHNOLOGY, Cheonan-si (KR)

( * ) Notice: Subject to any disclaimer, the term of this patent is extended or adjusted under 35 U.S.C. 154(b) by 300 days.

(21) Appl. No.: 16/918,311

(22) Filed: Jul. 1, 2020

(65) Prior Publication Data

US 2020/0331934 A1 Oct. 22, 2020

Related U.S. Application Data

(63) Continuation of application No. 16/404,740, filed on May 7, 2019, now Pat. No. 10,738,065.

(30) Foreign Application Priority Data

May 8, 2018 (KR) .......................... 10-2018-0052731

(51) Int. Cl.
  *C07D 301/02* (2006.01)
  *C07F 7/08* (2006.01)
  *B01J 31/02* (2006.01)

(52) U.S. Cl.
  CPC .......... *C07F 7/0801* (2013.01); *B01J 31/0267* (2013.01); *C07D 301/02* (2013.01); *B01J 2231/44* (2013.01); *B01J 2531/002* (2013.01)

(58) Field of Classification Search
  CPC .................................................. C07D 301/02
  USPC .......................................................... 549/215
  See application file for complete search history.

(56) References Cited

U.S. PATENT DOCUMENTS

| 9,670,309 B2 | 6/2017 | Chun et al. |
| 9,725,590 B2 | 8/2017 | Chun et al. |
| 9,732,182 B2 * | 8/2017 | Chun .................. C07D 303/12 |
| 2015/0361211 A1 | 12/2015 | Chun et al. |

FOREIGN PATENT DOCUMENTS

| JP | H06228252 A | 8/1994 |
| JP | 2007269965 A | 10/2007 |
| JP | 200984361 A | 4/2009 |
| JP | 2011095731 A | 5/2011 |
| JP | 2015180749 A | 10/2015 |
| JP | 2016511250 A | 4/2016 |
| KR | 101252063 B1 | 4/2013 |
| KR | 1020130111299 A | 10/2013 |
| KR | 1020140106441 A | 9/2014 |
| KR | 101596880 B1 | 2/2016 |
| KR | 101655857 B1 | 9/2016 |
| KR | 101840839 B1 | 3/2018 |
| KR | 101863111 B1 | 6/2018 |

OTHER PUBLICATIONS

Korean Office Action for Application No. 10-2018-0052731 dated Jun. 15, 2019.In conformance with MPEP 609—Concise explanation of the relevance includes issue date of KR OA and references cited therein.
Office Action(with no English translation) dated May 27, 2020 in JP 2019-088474 by the Japanese Patent Office.

* cited by examiner

*Primary Examiner* — Niloofar Rahmani
(74) *Attorney, Agent, or Firm* — Cantor Colburn LLP

(57) ABSTRACT

Provided is a method for preparing an epoxy compound having an alkoxysilyl group effectively by using a mild catalyst as well as an aromatic alcohol ring-opening agent. The preparation method for an epoxy compound having an alkoxysilyl group includes: performing a ring opening step by reacting an epoxy compound having an epoxide group, which is a starting material, with an aromatic alcohol ring-opening agent in the presence of a phosphine-based catalyst and an optional solvent so as to obtain an intermediate having a partially ring-opened epoxide group; and performing an alkoxysilylation step by reacting the intermediate having a partially ring-opened epoxide with isocyanate alkoxysilane.

10 Claims, 4 Drawing Sheets

PREPARATION METHOD FOR EPOXY COMPOUND HAVING ALKOXYSILYL GROUP

CROSS-REFERENCE TO RELATED APPLICATION(S)

This application claims priority to U.S. patent application Ser. No. 16/404,740, filed May 7, 2019, and Korean Patent Application No. 10-2018-0052731, filed on May 8, 2018 in the Korean Intellectual Property Office, and all the benefits accruing therefrom under 35 U.S.C. §§ 119, 120, the contents of which are incorporated herein by reference in their entirety.

BACKGROUND

1. Field

The present disclosure relates to a preparation method for an epoxy compound having an alkoxysilyl group using a mild catalyst, and more particularly, to a preparation method effectively for an epoxy compound having an alkoxysilyl group by using an aromatic alcohol as ring-opening agent in the presence of a mild catalyst.

2. Description of Related Art

Epoxy materials have good mechanical characteristics, electrically insulative characteristics, heat resistance, water resistance, adhesive characteristics, etc., and are thus widely used in applications such paintings, printed circuit boards, integrated circuit (IC) encapsulants, electric and electronic components, adhesives, and the like.

In applications such as semiconductor packaging, however, epoxy materials have problems such as coefficient of thermal expansion (CTE)-mismatch with silicon wafers caused by a large CTE of epoxy materials. Although research has been constantly conducted into methods of reducing the CTE of epoxy materials, the CTE of epoxy materials is still higher than required levels. For example, epoxy materials used in semiconductor packaging markedly limit the reliability and workability of semiconductor packages because the CTE of epoxy materials is higher than the CTE of silicon wafers. Therefore, the development of epoxy materials having improved thermal expansion characteristics has been required.

The inventors of the present application have developed epoxy compounds having an alkoxysilyl group as epoxy compounds having improved thermal expansion characteristics (Korean Patent Application Nos. 10-2012-0093320, 10-2013-0027308, 10-2013-0078347, 10-2013-0111473, 10-2014-0021884, etc.), and have observed that when an alkoxysilyl group was introduced into an epoxy compound, the heat resistance of an epoxy composite markedly increased.

In Korean Patent Application No. 10-2014-0021884 (Patent Registration No. 1655857) and Korean Patent Application No. 10-2013-0111473 (Patent Registration No. 1596880) that have been filed by the present inventors, an epoxy compound having an alkoxysilyl group is prepared, as shown in Reaction Scheme 1 below, through a first step (i) in which the epoxide group of an epoxy compound, a starting material is ring-opened by using a strong base such as NaOH, and a second step (ii) in which an alkoxysilyl group is introduced into the epoxy compound by alkoxysilylation.

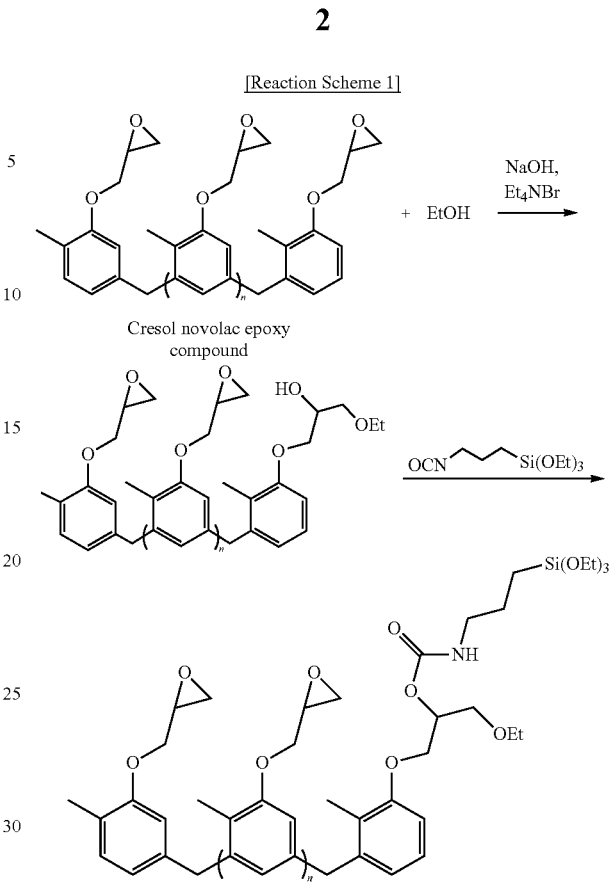

[Reaction Scheme 1]

Cresol novolac epoxy compound

In the methods of related art for preparing an epoxy compound having an alkoxysilyl group, (i) a strong base is used as a catalyst, and (ii) an excessive amount of a ring-opening agent is used to have the proper rate of the ring opening reaction in the first step. Due thereto, in the methods of the related art, (1) it is necessary to remove the strong base and the ring-opening agent used in the first step completely so as to prevent the strong base and the ring-opening agent from interrupting the alkoxysilylation in the second step. That is, after the reaction in the first process, purification (for example, workup) is performed, and then the second step is performed, thereby which increases manufacturing time and costs. In addition, (2) the molecular weight of the epoxy compound increases due to the ring opening step in which a strong base such as NaOH is used as a catalyst. Specifically, when a strong base such as NaOH is used in a ring opening process, highly reactive secondary alkoxide ions are formed as an intermediate product and consequently undergo side reactions, thereby producing an epoxy compound having a high molecular weight as a by-product. Furthermore, it gives the influenced on the degree of ring opening. In addition, (3) since a large amount of a ring-opening agent is used to ensure proper reactivity, the degree of ring opening has to be controlled by reaction time. Therefore, the time necessary for ring opening depend on the reaction conditions such as the structure of the epoxy compound, the scale of reaction, reaction concentrations, or reaction temperatures.

The present disclosure provides a preparation method for an epoxy compound having an alkoxysilyl group without the above-described problems that may occur when an epoxy compound having an alkoxysilyl group is prepared by a preparation method of the related art. That is, the present disclosure relates to a preparation method in which a mild catalyst is used to prepare an epoxy compound having an alkoxysilyl group in order to solve above-described problems with the preparation methods of the related art.

SUMMARY

An aspect of the present disclosure may include a preparation method for an epoxy compound having an alkoxysilyl group by using a mild catalyst and an aromatic alcohol as a ring-opening agent.

An aspect of the present disclosure may also provide a preparation method for an epoxy compound having an alkoxysilyl group where a ring opening step and an in-situ alkoxysilylation process can be performed continuously.

An aspect of the present disclosure may also provide a preparation method for an epoxy compound having an alkoxysilyl group where the degree of epoxy ring opening reaction is easy to control.

According to an aspect of the present disclosure, a preparation method for an epoxy compound having an alkoxysilyl group may include: a ring opening step is performed by reacting an epoxy compound having an epoxide group, a starting material with an aromatic alcohol ring-opening agent in the presence of a phosphine-based catalyst and an optional solvent so as to obtain an intermediate product having a partially ring-opened epoxide group; and performing an alkoxysilylation step by reacting the intermediate product having a partially ring-opened epoxide group with isocyanate alkoxysilane.

The in situ alkoxysilylation step may be carried out continuously following the ring opening step.

The ring opening step may not require subsequent purification of the intermediate product having a partially ring-opened epoxide group.

The epoxy compound having an epoxide group, which is a starting material, may include at least one selected from the group consisting of Formulae AS to IS below:

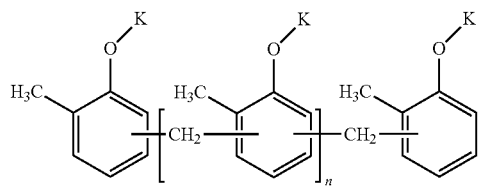
(AS)

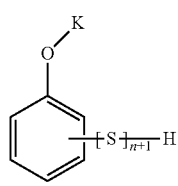
(BS)

-continued

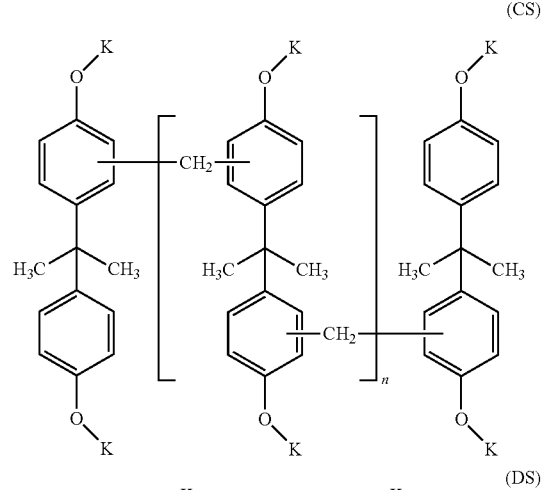
(CS)

(DS)

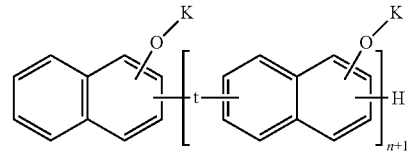
(ES)

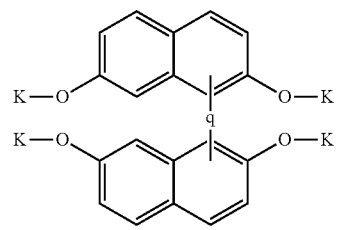
(FS)

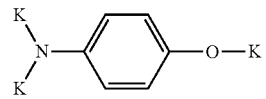
(GS)

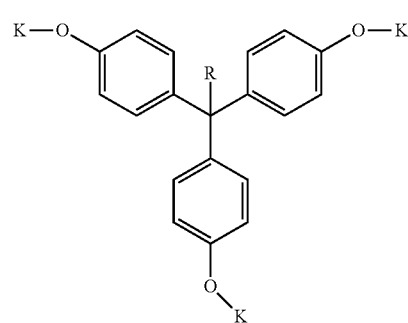

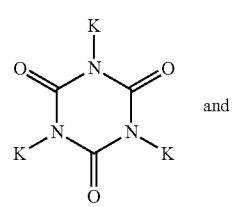 and
(HS)

-continued

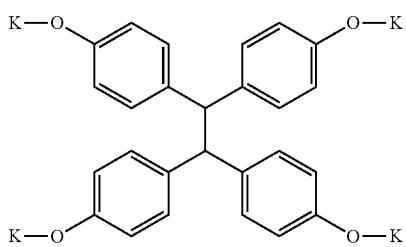

wherein in Formula BS, S is

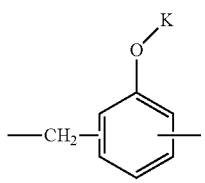

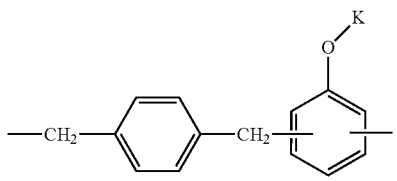

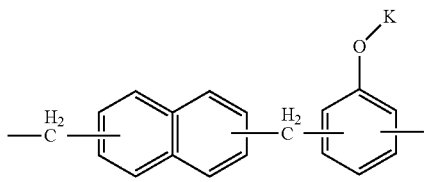

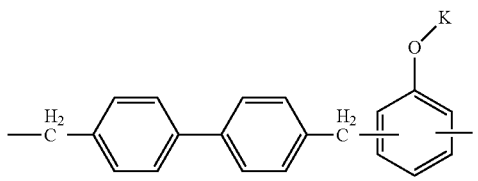

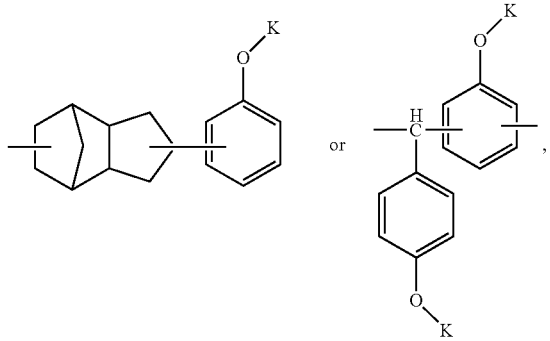

in Formula DS, t is

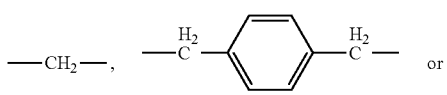

(IS) 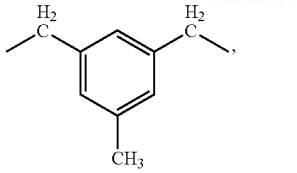

in Formulae AS to DS, n is an integer equal to or greater than 1 or ranging from 1 to 30, in Formula ES, -q- is —CH$_2$— or a direct linkage, in Formula GS, R is hydrogen, a hydroxyl group, a C1 to C10 alkyl group, or a C6 or C10 aromatic group, and in Formulae AS to IS, at least three of Ks are structures having an epoxide group of Formula E1 below, and remaining Ks are hydrogen.

(E1)

$$\underset{O}{\triangle}\!\!-\!CH_2\!-$$

The aromatic alcohol ring-opening agent may include at least one selected from the group consisting of Formulae 1 and 2 below:

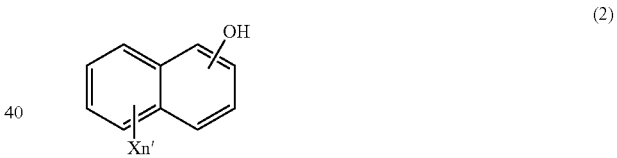

wherein in Formulae 1 and 2, each X is independently selected from the group consisting of H, a C1 to C10 alkyl group, an allyl group, a C6 or C10 aryl group (the C6 or C10 aryl group may be substitutable with a C1-C3 alkyl group), a C1 to C5 alkoxy group, a nitro group, or a halogen selected from the group consisting of F, Cl, Br and I, and n' is an integer ranging from 1 to 5.

The phosphine-based catalyst may be represented by Formula A below:

PRxRyRz         [Formula A]

wherein Rx, Ry, and Rz are each independently a C1-C10 alkyl group, a C1-C10 alkoxy group, a C6 or C10 aryl group, a C6-C10 cycloalkyl group, or a tertiary amine group.

0.05 to 0.9 equivalents of the aromatic alcohol ring-opening agent may be used per 1 equivalent of the epoxide group of the epoxy compound which is a starting material.

0.1 to 2 parts by weight of the phosphine-based catalyst may be used per 100 parts by weight of the epoxy compound which is a starting material.

The ring opening step may be performed at a temperature of 60° C. to 200° C.

The ring opening step may be performed for 10 minutes to 48 hours.

BRIEF DESCRIPTION OF DRAWINGS

The above and other aspects, features and other advantages of the present disclosure will be more clearly understood from the following detailed description taken in conjunction with the accompanying drawings, in which.

DETAILED DESCRIPTION

Figure 1:
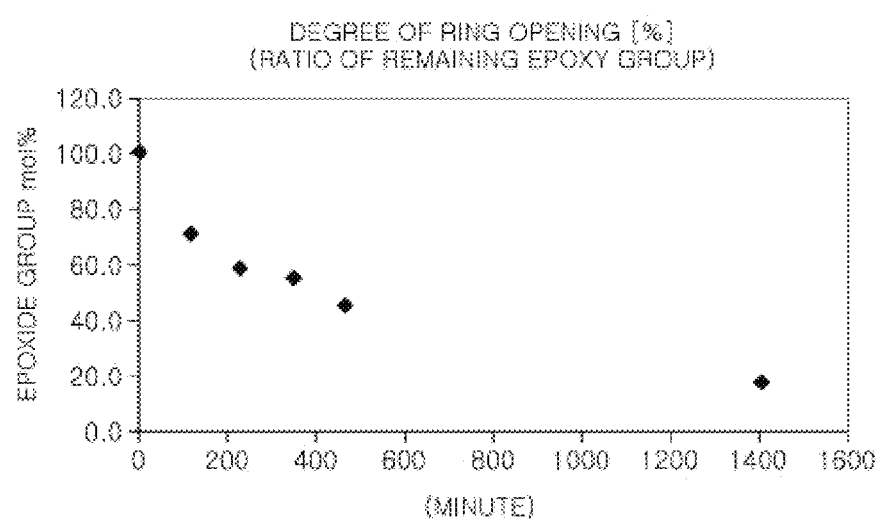
FIG. 1 is a graph showing the degree of ring opening as a function of time in Comparative Synthesis Example 2.

The present disclosure provides a simple and efficient preparation method for an epoxy compound having an alkoxysilyl group. According to the present disclosure, an epoxy compound having an alkoxysilyl group is prepared by ring opening of the epoxide group of an epoxy compound using a mild catalyst and an aromatic alcohol ring-opening agent and subsequent alkoxysilylation of the hydroxy group formed from the ring-opened epoxy compound.

According to an embodiment of the present disclosure, an epoxy compound having an alkoxysilyl group is prepared through a step (ring opening process, the first step) in which an epoxy compound having an epoxide group, a starting material reacts with a ring-opening agent in the presence of a mild catalyst and an optional solvent so as to open a part of the epoxy ring and obtain an intermediate product having a partially ring-opened epoxide group; and a (alkoxysilylation step, the second step) in which the intermediate product having a partially ring-opened epoxide group reacts with isocyanate alkoxysilane.

According to another embodiment of the present disclosure, in the preparation method of the present invention, the in situ alkoxysilylation step may be continuously performed following the ring-opening process. That is, according to the preparation method of the present disclosure, after the intermediate product having a partially ring-opened epoxide group is obtained through the ring opening process, the in situ alkoxysilylation step may be continuously performed using the intermediate product having a partially ring-opened epoxide group to prepare the epoxy compound having an alkoxysilyl group. The alkoxysilylation reaction is performed without an additional purification for the intermediate product.

According to another embodiment of the present disclosure, an epoxy compound having an alkoxysilyl group is prepared by reacting an epoxy compound having an epoxide group, a starting material with a ring-opening agent in the presence of a mild catalyst and an optional solvent so as to obtain a partially epoxide ring-opened intermediate product (ring opening process), and subsequently adding isocyanate alkoxysilane in situ to the partially epoxide ring-opened intermediate product so as to alkoxysilylate the hydroxy group of the partially ring-opened intermediate product (alkoxysilylation step).

In the preparation method of the present disclosure, the overall reaction mechanism of the epoxy compound having an alkoxysilyl group may be, for example, as shown in Reaction Scheme 2 below.

[Reaction Scheme 2]

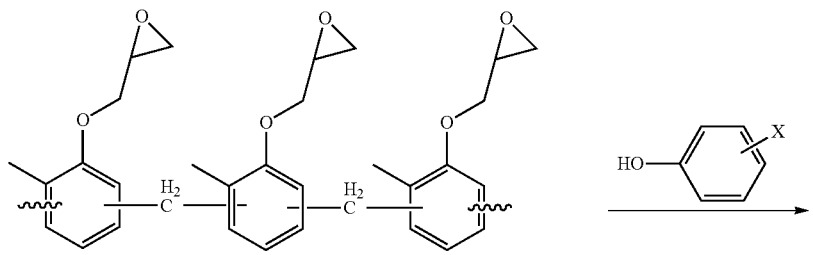

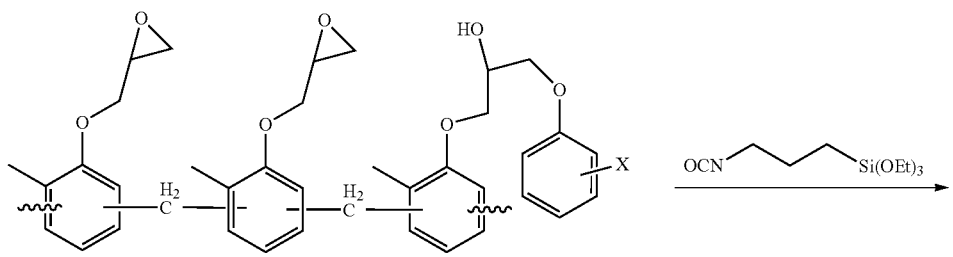

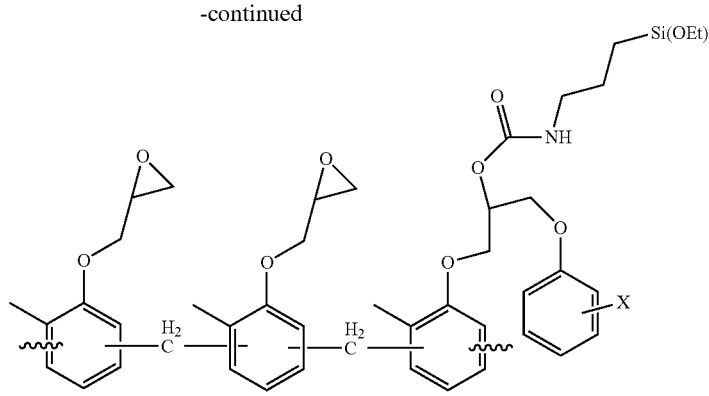

First, in the ring opening process, an epoxy compound having an epoxide group, a starting material reacts with a ring-opening agent in the presence of a mild catalyst and an optional solvent so as to open the a part of ring of the epoxide group and obtain an intermediate product having a partially ring-opened epoxide group.

The starting-material, epoxy compound having an epoxide group may be an epoxy compound having at least three epoxide groups. The starting epoxy compound may be any epoxy compound having three or more epoxide groups which is known in the related art. Examples of the epoxy compound having three or more epoxide groups include a glycidyl ether type epoxy compound, a glycidyl type epoxy compound, a glycidyl amine type epoxy compound, and a glycidyl ester type epoxy compound. More specifically, the epoxy compound having three or more epoxide groups may have, as a core, a bisphenol, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, alicyclic, aliphatic, or novolac unit.

More specifically, the epoxy compound having three or more epoxide groups may be one selected from the group consisting of Formulae AS to IS below:

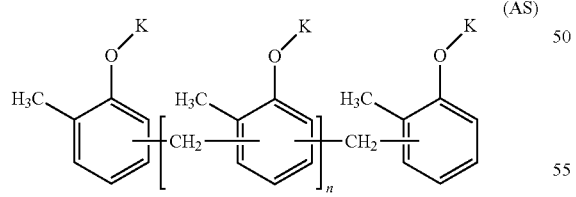
(AS)

(BS)

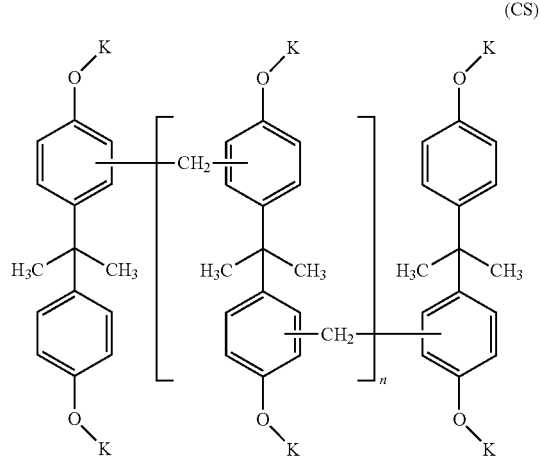
(CS)

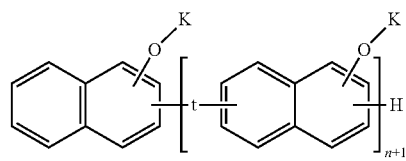
(DS)

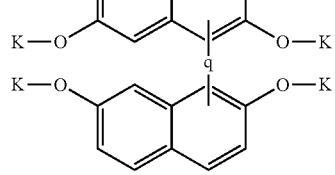
(ES)

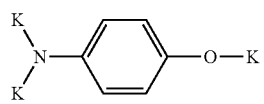
(FS)

-continued

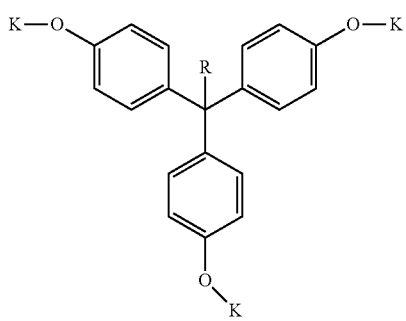
(GS)

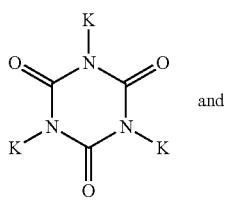
and

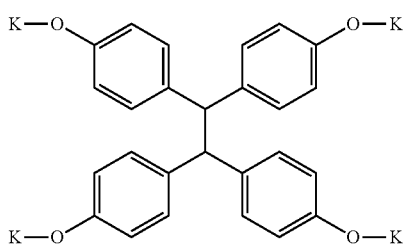

In Formula BS, S is

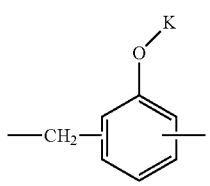

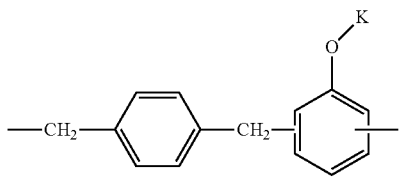

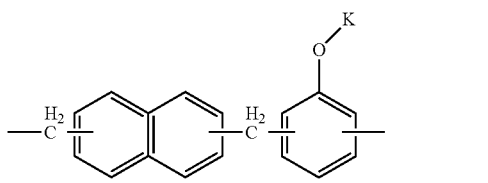

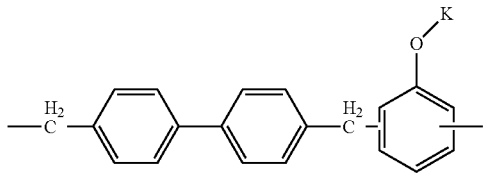

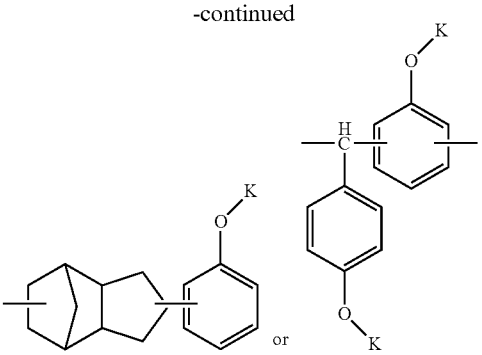
(HS)

or

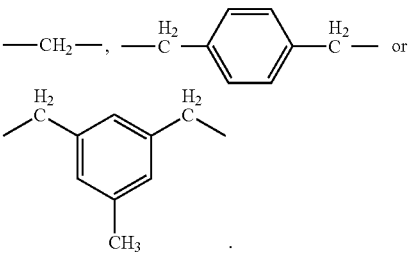
(IS)

(DS)

In Formula DS, t is

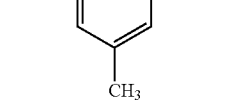, 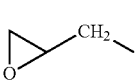 or

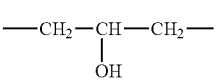

In Formulae AS to DS, n is an integer equal to or greater than 1, preferably within the range of 1 to 30.

In Formula ES, -q- is —$CH_2$— or a direct linkage.

In Formula GS, R is hydrogen, a hydroxyl group, a C1 to C10 alkyl group, or a C6 or C10 aromatic group (aryl group).

In Formulae AS to IS, at least three of Ks may be structures having an epoxide group of Formula E1 below, and the remaining Ks may be hydrogen.

$$\underset{O}{\triangle}\text{—CH}_2\text{—} \qquad (E1)$$

At least two identical structures of a formula selected from the group consisting of Formulae ES to IS may be connected to each other, and in this case, the structures may form a polymer where the structures are connected to each other at positions of some Ks via a linker having a hydroxyl group such as Formula LG1 below. For example, when two structures of Formula ES are connected to each other, one of Ks for one structure with Formula ES may be connected to one of Ks of the other structure with Formula ES by the unit of Formula LG1 below:

$$\text{—CH}_2\text{—CH(OH)—CH}_2\text{—} \qquad (LG1)$$

Non-limiting example of the ring-opening agent may include aromatic alcohols, more specifically, phenols and naphthols respectively, represented by Formulae 1 and 2 below. That is, at least one selected from the group consisting of phenols and naphthols of Formulae 1 and 2 below may be used as the ring-opening agent.

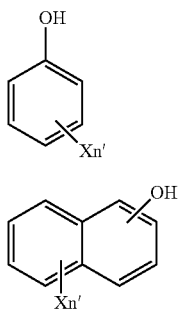

(1)

(2)

In Formulae 1 and 2 above, each X may be independently selected from the group consisting of H, a C1 to C10 alkyl group, an allyl group, a C6 or C10 aryl group (the C6 or C10 aryl group may be substituted with a C1-C3 alkyl group), a C1 to C5 alkoxy group, a nitro group, and a halogen selected from the group consisting of F, Cl, Br and I, and n' is an integer ranging from 1 to 5.

A phosphine-based catalyst represented by Formula A below may be used as the mild catalyst.

$$PR_xR_yR_z \qquad \text{[Formula A]}$$

where Rx, Ry and Rz may each independently be a C1-C10 alkyl group, a C1-C10 alkoxy group, a C6 or C10 aryl group, a C6-C10 cycloalkyl group, or a tertiary amine group. The tertiary amine group may specifically be $-N(C_{n''}H_{2n''+1})_3$ where n" may be an integer ranging from 1 to 10.

In a non-limiting example, the mild catalyst of Formula A may include at least one selected from the group consisting of triphenylphosphine (TPP), diphenyl propyl phosphine, and tricyclohexylphosphine.

In the ring opening process, an aromatic alcohol used as the ring-opening agent is stoichiometrically reacted with the epoxide group of the starting-material epoxy compound in the presence of the phosphine-based catalyst. Therefore, the degree of ring opening of the epoxide group may be easily controlled by adjusting the equivalent of the aromatic alcohol.

The aromatic alcohol ring-opening agent may be used in an amount of 0.05 to 0.9 equivalents, more preferably 0.05 to 0.7 equivalents, and still more preferably 0.05 to 0.5 equivalents per 1 equivalent of the epoxide group of the starting material, epoxy compound. If less than 0.05 equivalents of the aromatic alcohol ring-opening agent (specifically, a hydroxy group of the aromatic alcohol) is used per 1 equivalent of the epoxide group of the starting material, ring opening occurs poorly. In addition, since the stoichiometric equivalent ratio of aromatic alcohol and epoxide group is 1:1, if the aromatic alcohol is used in an amount of 1 equivalent or greater, the epoxide group does not remain in a final product. Thus, it may not be preferably to use 1 equivalent or greater of the aromatic alcohol. Therefore, preferably, the aromatic alcohol ring-opening agent may be used in an amount of 0.9 equivalents or less so that the epoxide group may remain in the final product, that is, in the epoxy compound having an alkoxysilyl group.

The phosphine-based catalyst used as the mild catalyst may be used in an amount of 0.1 wt % to 2 wt %, and preferably 0.5 wt % to 1 wt % based on the weight of the starting-material epoxy compound (that is, in an amount of 0.1 to 2 parts by weight, and preferably 0.5 to 1 part by weight per 100 parts by weight of the starting-material epoxy compound). If the amount of the phosphine-based catalyst is less than 0.1 wt %, the rate of reaction may be markedly low, and thus ring opening may occur poorly. However, even if the amount of the phosphine-based catalyst is greater than 2 wt %, an additional increase in the rate of reaction is not observed, and thus it may not be preferable to use the phosphine-based catalyst in an amount of greater than 2 wt %.

The reaction temperature and the reaction time of the ring opening step depend on the kinds of reactants. However, for example, the reaction temperature of the ring opening step may be adjusted to be within the range of 60° C. to 200° C., and more preferably within the range of 80° C. to 150° C. If the reaction temperature is less than 60° C., the rate of reaction may be markedly low, and thus ring opening may occur poorly. Conversely, if the reaction temperature exceeds 200° C., the stability of the epoxide group may be affected. Thus, the reaction temperature may preferably be adjusted to be within the above-mentioned range. The reaction time of the ring opening step may be from 10 minutes to 48 hours, and more preferably from 10 minutes to 24 hours. Although the optimal reaction time varies depending on the structure and the degree of ring opening of the epoxide group, the amount of the catalyst, and the amount of a solvent, if the reaction time is less than 10 minutes, the ring opening reaction may not proceed sufficiently. When the reaction time is 48 hours, the ring opening reaction proceeds sufficiently, and thus additional reaction is not needed.

The ring of the epoxide group of the starting-material epoxy compound is opened through the above-described ring opening process, and thus an intermediate product is obtained.

In the ring opening reaction, a solvent may be optionally used if needed. For example, if the viscosity of the reactants is suitable for reaction at a given reaction temperature in the ring opening process, a solvent may not be used. That is, if the viscosity of the reactants is sufficiently low to mix and agitate the reactants, a solvent may not be additionally used. This could be easily determined by a person of ordinary skill in the art. When a solvent is used, any organic solvent (aprotic solvent) may be used as long as the organic solvent easily dissolves the reactants, does not have any negative influence on reactions, and is easily removed after reactions. Non-limiting examples of the solvent may include acetonitrile, tetra hydro furan (THF), methyl ethyl ketone (MEK), dimethyl formamide (DMF), dimethyl sulfoxide (DMSO), toluene, and xylene. These solvents may be used alone or in combination of two or more. The amount of the solvent is not particularly limited. For example, the solvent may be used in a proper amount for sufficiently dissolving the reactants without any negative influence on reactions, and this could be easily determined by a person of ordinary skill in the art.

The ring of the epoxide group of the starting material is opened through the ring opening reaction (the first reaction in Reaction Scheme 2), and thus the intermediate product is obtained. Specifically, the intermediate product may be represented by one selected from the group consisting of Formulae AM to IM.

[Structural Formulae of Intermediate Products]
(AM)
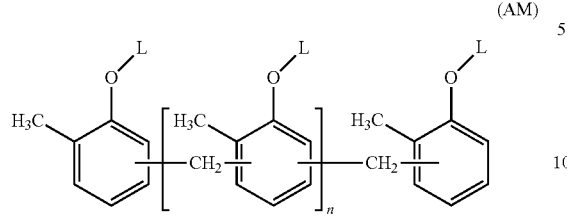
(BM)
(CM)
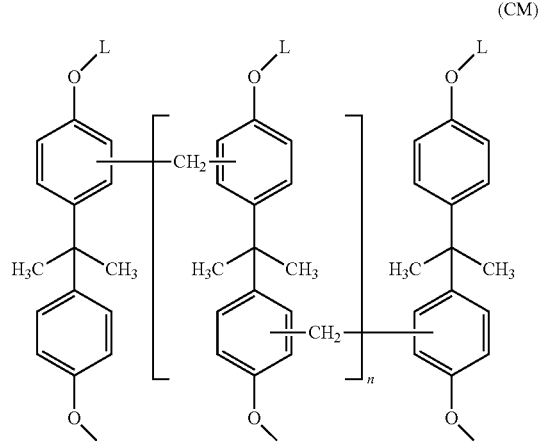
(DM)
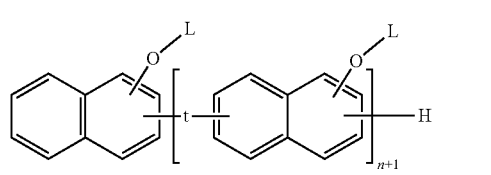
(EM)
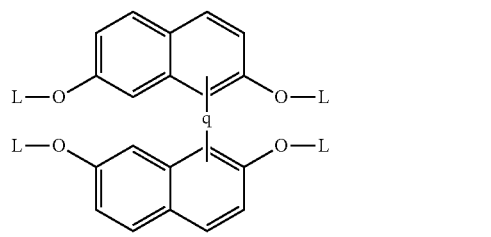
(FM)
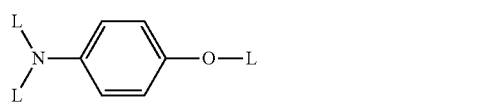
(GM)
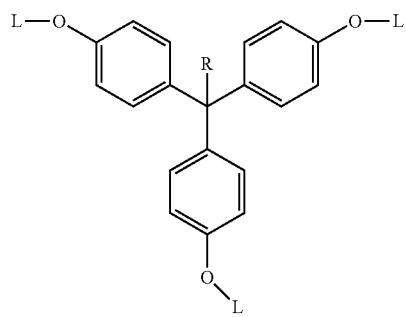
(HM)
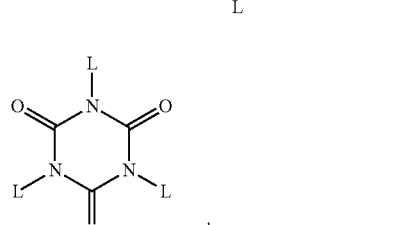
and
(IM)
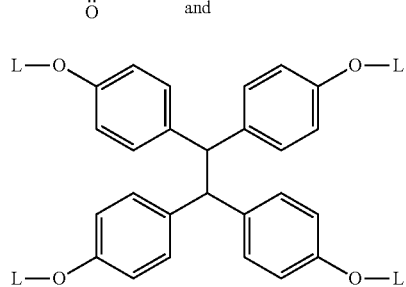
In Formula BM, S is
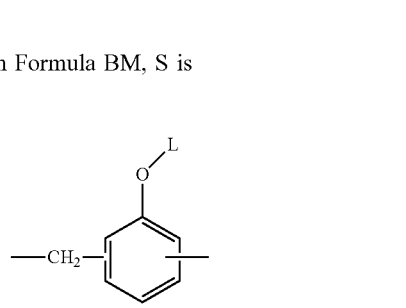
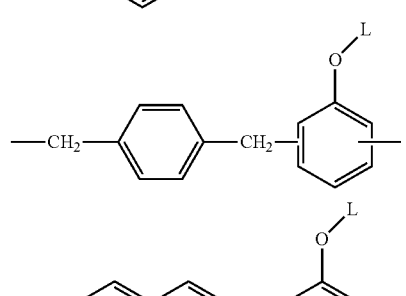
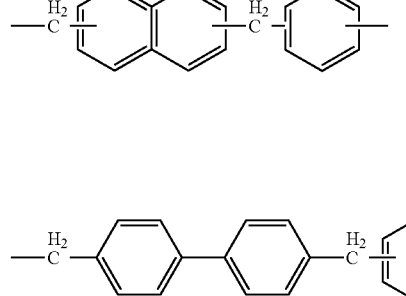

-continued

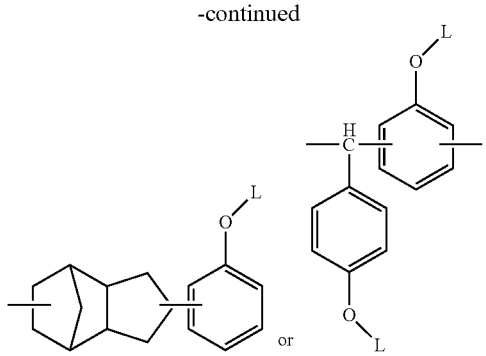

In Formula DM, t is

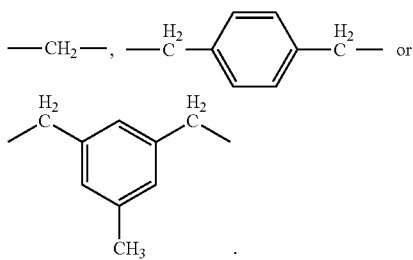

In Formulae AM to DM, n is an integer equal to or greater than 1, preferably an integer ranging from 1 to 30.

In Formula EM, -q- is —CH$_2$— or a direct linkage,

In Formula GM, R is hydrogen, a hydroxyl group, a C1-C10 alkyl group, or a C6 or C10 aromatic group, In Formulae AM to IM, at least one of Ls is

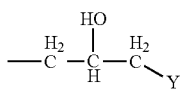

where Y is represented by Formula 3 or 4 below:

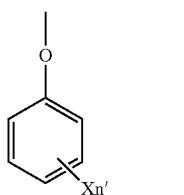

(3)

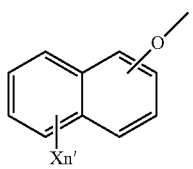

(4)

where Formulae 3 and 4 above, each X may be independently selected from the group consisting of H, a C1 to C10 alkyl group, an allyl group, a C6 or C10 aryl group (the C6 or C10 aryl group may be substituted with a C1-C3 alkyl group), a C1 to C5 alkoxy group, a nitro group, and a halogen selected from the group consisting of F, Cl, Br and I, and n' is an integer ranging from 1 to 5; at least two of Ls may be structures having an epoxide group of Formula E1, and remaining of Ls may be hydrogen.

When two or more structures represented by one selected from the group consisting of Formulae EM to IM are connected to each other, the structures may be connected to each other at one of Ls through a linker having a hydroxyl group of Formula LG1 above. For example, when two structures represented by Formula EM are connected to each other, one of Ls of one of the two structures is connected to one of Ls of the other of the two structures by the structure of Formula LG1 above.

Since the aromatic alcohol undergoes reaction stoichiometrically with the epoxy compound in the presence of the phosphine-based catalyst which is a mild catalyst, the degree of ring opening of the epoxide group may be easily controlled according to the equivalent of the aromatic alcohol.

In addition, unlike NaOH as a ring-opening agent in the related art, in the method of the present disclosure, a strong base affecting the second reaction step is not used in the ring opening process, and thus a purification step is not required after the ring opening process. The purification step may be, for example, a workup process.

In the alkoxysilylation step (the second reaction in Reaction Scheme 2), the intermediate product obtained in the ring opening step reacts with isocyanate alkoxysilane, and thus an alkoxysilyl group is introduced into the hydroxy group of the intermediate product, thereby obtaining an epoxy compound having an alkoxysilyl group.

The isocyanate alkoxysilane used in the alkoxysilylation step may be represented by Formula B below.

$$OCN(CH_2)_3SiR_1R_2R_3 \qquad \text{[Formula B]}$$

where at least one of $R_1$ to $R_3$ is a C1-C5 alkoxy group, preferably a C1-C3 alkoxy group, and the others are C1-C10 alkyl groups.

In addition, the alkoxysilylation reaction of the hydroxy group is performed in the presence of a base catalyst. Examples of the base catalyst may include, but are not limited to, $K_2CO_3$, $Na_2CO_3$, $KHCO_3$, $NaHCO_3$, and amines. Specific examples of the amines include triethylamine, diisopropylethylamine, and pyridine. Strong bases such as NaOH or KOH are not used because such strong bases participate in an epoxy ring opening reaction and react with isocyanate alkoxysilane to cause side reactions.

These base catalysts may be used alone or in combination of two or more. 0.5 to 1 equivalent of the base catalyst may be used per 1 equivalent of the hydroxyl group of the epoxy compound (the intermediate product obtained through the first process) in terms of reaction efficiency. If less than 0.5 equivalents of the base catalyst are used, the catalytic activity for the reaction may be insufficient in reaction, and intended catalytic activity may be obtained by adding 1 equivalent of the base catalyst, and thus, no excessive excess thereof is required.

In the above reaction, the epoxy compound having a hydroxy group (the intermediate product in the first process) and the isocyanate alkoxysilane may be reacted with each other at a proper ratio according to an intended degree of alkoxysilylation of the hydroxy group of the intermediate product because the hydroxyl group of the epoxy compound and the alkoxysilane group of the isocyanate alkoxysilane react with each other at a stoichiometric equivalent ratio. That is, the degree of alkoxysilylation may be controlled in this manner. For example, 0.1 to 1.2 equivalents, preferably 0.3 to 1.0 equivalents, and more preferably 1 equivalent of isocyanate alkoxysilane may be reacted with 1 equivalent of the hydroxyl group of the epoxy compound. For example, if the amount of isocyanate alkoxysilane is less than 0.1 equivalents, the alkoxysilyl group of the final product is insufficient. However, if the amount of isocyanate alkoxysilane is 1.2 equivalents, alkoxysilylation occurs sufficiently, and thus it is not needed to use isocyanate alkoxysilane more than 1.2 equivalents.

Although the reaction temperature and time of the reaction in the second step vary according to the reactants, since the reaction rate (reactivity) of the hydroxyl group of the epoxy compound is markedly low at a low temperature, the reaction temperature may preferably be adjusted to be 40° C. or greater. In addition, if the reaction temperature is greater than 150° C., the thermal stability of the reactants may decrease during the reaction. Therefore, the reaction temperature in the second step may be adjusted to be within the range of 40° C. to 150° C.

The reaction time in the second step may be adjusted to be within the range of 6 hours to 120 hours, and preferably for 12 hours to 72 hours. If the reaction time is less than 6 hours, the alkoxysilylation of the hydroxyl group may insufficiently occur, and if the reaction time is greater than 120 hours, it is not preferable because additional reaction does not occur. Therefore, the reaction time may be adjusted to be within the range of 6 hours to 120 hours to alkoxysilylate the hydroxyl group without insufficient reaction of the hydroxyl group or unnecessary continuation of the reaction.

In the alkoxysilylation process, a solvent may be optionally used if needed. For example, if the viscosity of the reactants is suitable for reaction at a given reaction temperature, a solvent may not be used. That is, if the viscosity of the reactants is sufficiently low to mix and agitate the reactants, a solvent may not be additionally used. This could be easily determined by a person of ordinary skill in the art. However, if the use of a solvent is needed, any aprotic solvent may be used as long as the aprotic solvent easily dissolves the reactants without any influence on the reaction and the solvent is easily removed after the reaction. Non-limiting examples of the solvent may include toluene, xylene, acetonitrile, tetra hydro furan (THF), methyl ethyl ketone (MEK), dimethyl formamide (DMF), dimethyl sulfoxide (DMSO), and methylene chloride (MC). These solvents may be used alone or in combination of two or more. The amount of the solvent is not particularly limited. For example, the solvent may be used in a proper amount for sufficiently dissolving the reactants without any negative influence on the reaction, and this could be easily determined by a person of ordinary skill in the art.

Specifically, the epoxy compound having an alkoxysilyl group and prepared by the preparation method of the present disclosure may be represented by Formulae AF to IF below. That is, an epoxy compound having an alkoxysilyl group and represented by one of Formulae AF to IF may be prepared by the preparation method of the present disclosure.

(AF)
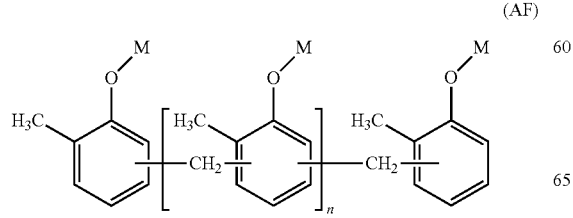

-continued (BF)
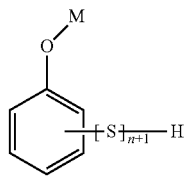

(CF)
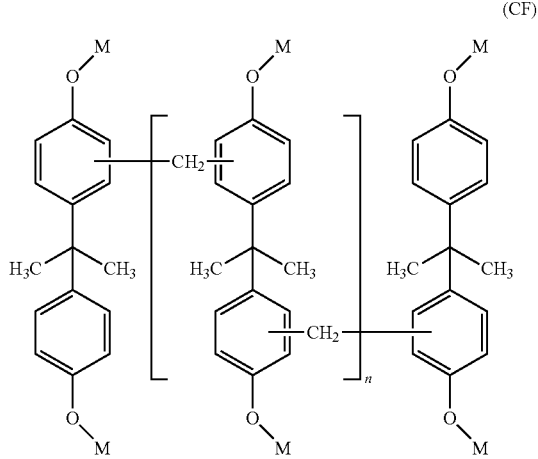

(DF)
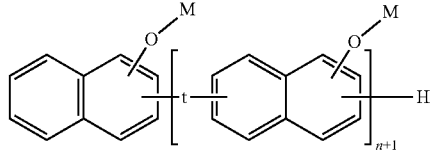

(EF)
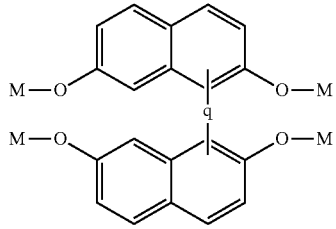

(FF)
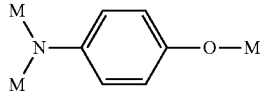

(GF)
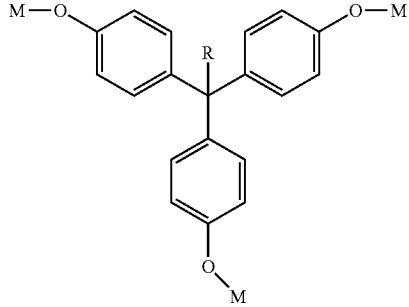

-continued

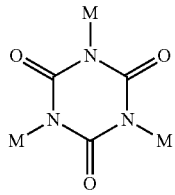

and

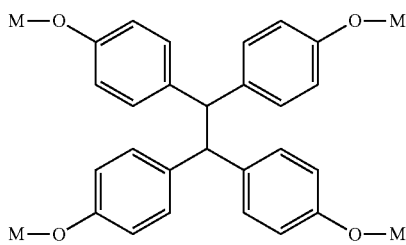

In Formula BF, S is

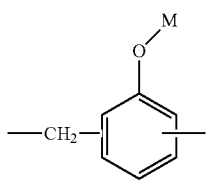

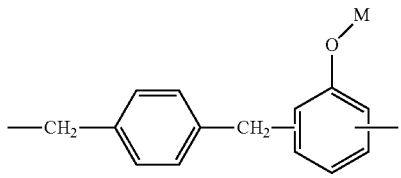

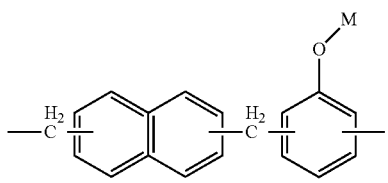

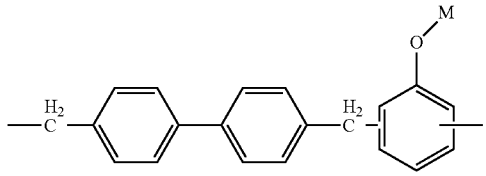

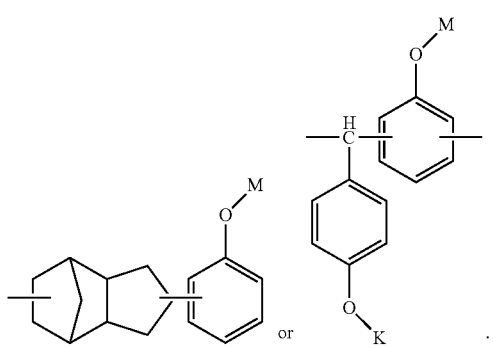

In Formula DF, t is

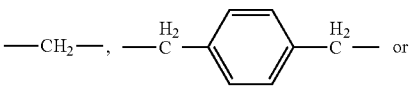

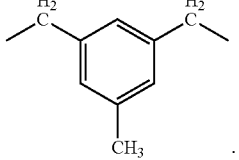

In Formulae AF to DF, n is an integer equal to or greater than 1, preferably an integer ranging from 1 to 30.

In Formula EF, -q- is —$CH_2$— or a direct linkage.

In Formula GF, R is hydrogen, a hydroxyl group, a C1-C10 alkyl group, or a C6 or C10 aromatic group.

In Formula AF to IF, at least one of Ms is

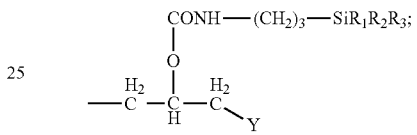

where Y is represented by Formula 3 or 4 below;

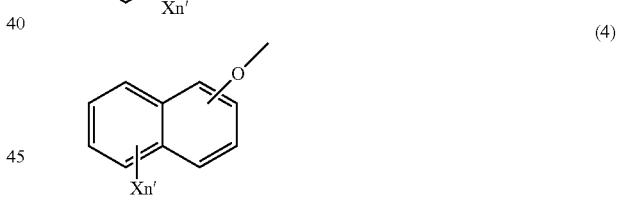

where Formulae 3 and 4 above, each X may be independently selected from the group consisting of H, a C1 to C10 alkyl group, an allyl group, a C6 or C10 aryl group (the C6 or C10 aryl group may be substituted with a C1-C3 alkyl group), a C1 to C5 alkoxy group, a nitro group, and a halogen selected from the group consisting of F, Cl, Br and I, and n' is an integer ranging from 1 to 5;

at least one of $R_1$ to $R_3$ may be a C1-C5 alkoxy group, preferably a C1-C3 alkoxy group, and the others may be C1-C10 alkyl groups; at least two of Ms may be structures having an epoxide group of Formula E1, and the remaining of Ms may be hydrogen.

When two or more structures represented by one selected from the group consisting of Formulae EF to IF are connected to each other, the structures may be connected to each other at one of Ms through a linker having a structure of Formula LG1 above or an alkoxysilyl group of Formula LG2 below. For example, when two structures having Formula EF are connected to each other, one of Ms of one of the two structures is connected to one of Ms of the other of the two structures by the structure of Formula LG1 above or Formula LG2 below:

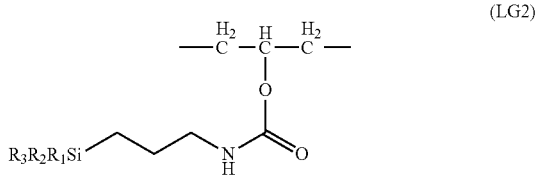

(LG2)

In Formula LG2, at least one of $R_1$ to $R_3$ is a C1-C5 alkoxy group, preferably a C1-C3 alkoxy group, and the others are C1-C10 alkyl groups.

The epoxy compound having an alkoxysilyl group and prepared by the method of the present disclosure is applicable to any fields, applications, uses to which epoxy compounds of the related art are applicable. For example, the epoxy compound having an alkoxysilyl group is not limited to these, but may be used in combination with for example, a curing agent, a filler (inorganic particles and/or fibers), a curing accelerator (catalyst), or any other general compound (epoxy resin). The curing agent and the filler may be any curing agent and any filler known in the related art as being used together with epoxy compounds (resins).

For example, the epoxy compound having an alkoxysilyl group may be used in various applications, but not limited to, such as electronic materials, semiconductor substrates, IC substrates, laminates in which a metal layer is provided on a base layer, prepreg, encapsulants (packaging materials), printed circuit boards, electronic components, adhesives, paintings, composite materials, and the like. In addition, the epoxy compound having an alkoxysilyl group and prepared by the method of the present disclosure has high heat resistance. In particular, a composite material including the epoxy compound and a filler may have high heat resistance.

Hereinafter, the method of preparing an epoxy compound having an alkoxysilyl group of the present disclosure will be specifically described through examples.

A. SYNTHESIS EXAMPLES

Synthesis Example 1

25 g of a cresol novolac epoxy compound (Structural Formula 1, EEW=220, epoxide concentration=0.114 mol), and 2.14 g (0.023 mol) of phenol were added to 25 g of toluene in a two-necked flask and were stirred for 10 minutes at room temperature (about 20° C. to 26° C., the same applies hereinafter). Thereafter, 0.25 g of TPP was added to the flask, and the flask was heated to 110° C. for 12 hours to open the epoxide ring. The end of the ring opening reaction was confirmed by performing a nuclear magnetic resonance (NMR) analysis using a sample slightly taken out of the reaction flask. After this step, the temperature of the flask was lowered to 80° C., and 2.94 g of N,N-diisopropylethylamine (DIPEA) and 5.62 g (0.023 mol) of 3-(triethoxysilyl)propyl isocyanate were added to the flask, and then, the flask was further heated and stirred for 12 hours. Thereafter, the flask was cooled to room temperature, and the N,N-diisopropylethylamine and the solvent were removed using a rotary evaporator. Then, after drying using a vacuum pump, a final product was obtained. An epoxy compound having an alkoxysilyl group thus obtained had an [epoxide group]:[alkoxysilyl group] mole ratio of 4:1 and an epoxy equivalent weight (EEW) of 361 g/Eq.

In Synthesis Example 1, after the ring opening reaction, alkoxysilylation was performed in situ without a separate workup process, and the epoxy compound having an alkoxysilyl group was obtained.

[Structural Formula 1]

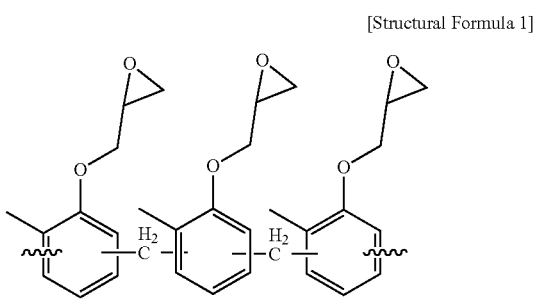

[NMR of Starting Material]
$^1$H NMR (400 MHz, DMSO): δ=7.08-6.55 (m, 30.87H), 4.30-3.39 (m, 52.75H), 3.35-3.04 (m, 12.97H), 2.86-2.59 (m, 28.68H), 2.26-1.95 (m, 45.00H)

[NMR of Intermediate Product after Ring Opening Reaction]
$^1$H NMR (400 MHz, DMSO): δ=7.08-6.55 (m, 43.87H), 4.30-3.39 (m, 60.35H), 3.35-3.04 (m, 10.13H), 2.86-2.59 (m, 23.33H), 2.26-1.95 (m, 45.00H)

[NMR of Final Product]
$^1$H NMR (400 MHz, DMSO): δ=7.07-6.56 (m, 43.47H), 4.29-3.39 (m, 76.30H), 3.33-3.05 (m, 10.00H), 3.02-2.87 (m, 5.84H), 2.84-2.58 (m, 12.72H), 2.25-1.93 (m, 43.64H), 1.58-1.36 (m, 5.04H), 1.16-0.98 (m, 24.08H), 0.57-0.41 (m, 5.35H)

The concentrations of the epoxide group and the alkoxysilyl group in each reaction step were determined from the NMR results as shown in Table 1 below. After adding phenol (2.14 g, 0.023 mol) corresponding to about 20 mol % of the epoxide group of the cresol novolac epoxy compound (25 g, 0.114 mol), it was observed that about 20 mol % of the epoxide group was ring-opened. In other words, it was confirmed that the number of epoxide groups was decreased corresponding to the equivalent of the ring-opening agent (phenol) used in the reaction. That is, the ring opening reaction occurred stoichiometrically. In addition, by comparing the NMR of starting material with the intermediate after the ring opening reaction and NMR results in each reaction process, it was observed that by-products were not formed during the reaction.

TABLE 1

Concentration of each functional group in each reaction step (results of NMR)

| H-value of NMR peak | |
|---|---|
| Epoxide group* | Alkoxysilyl group** |
| (@ 3.35-3.04 ppm) | (@ 0.57-0.41 ppm) |

TABLE 1-continued

| Reaction step | * | ** | Remarks |
|---|---|---|---|
| (a) Starting material | 12.97 | — | |
| (b) Intermediate product (after ring opening reaction in first process) | 10.13 | — | Concentration of epoxide functional group: decrease by about 20 mol % |
| (c) Final product (in second process) | 10.10 (1H) | 5.35 (2H) | [epoxy]:[silyl group] = 0.8:0.2 |

Synthesis Example 2

In Synthesis Example 2, a biphenyl-based novolac epoxy compound having an alkoxysilyl group was obtained by performing reactions in the same manner as in Synthesis Example 1 except that a biphenyl-based novolac epoxy compound of Structural Formula 2 below was used as a starting material, and the concentrations of materials were adjusted as shown in Table 2 below. The [epoxide group]:[alkoxysilyl group]mole ratio of the final product was 4:1, and the EEW of the final product was 424.

TABLE 2

Content of materials used in Synthesis Example 2

| | Ring opening process | | | Alkoxysilylation process | | |
|---|---|---|---|---|---|---|
| | Biphenyl-based novolac epoxy (EEW = 271) | TPP | Phenol | 3-(triethoxysilyl)propyl isocyanate | N,N-diisopropyl-ethylamine | Toluene |
| Synthesis Example 2 | 25 g (0.092 mol) | 0.25 g | 1.73 g (0.018 mol) | 4.56 g (0.018 mol) | 2.38 g | 25 g |

[NMR of Final Product]

$^1$H NMR (400 MHz, DMSO): δ=7.53-6.87 (m, 94.65H), 4.31-4.22 (m, 8.09H), 4.03-3.27 (m, 41.23H), 3.00-2.90 (m, 4.00H), 2.83-2.78 (m, 7.84H), 2.70-2.66 (m, 8.21H), 1.56-1.38 (m, 3.99H), 1.17-1.12 (m, 20.25H), 0.57-0.50 (m, 3.86H)

[Structural Formula 2]

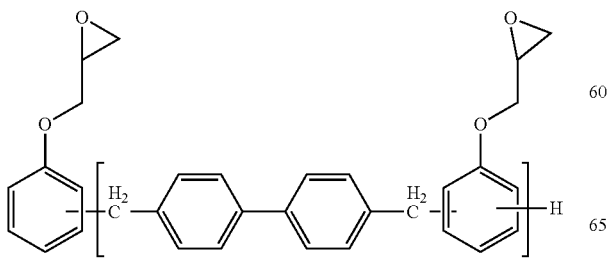

Synthesis Example 3

In Synthesis Example 3, a bisphenol A-based novolac epoxy compound having an alkoxysilyl group was obtained by performing reactions in the same manner as in Synthesis Example 1 except that a bisphenol A-based novolac epoxy compound of Structural Formula 3 below was used as a starting material, and the concentrations of materials were adjusted as shown in Table 3 below. The [epoxide group]:[alkoxysilyl group] mole ratio of the final product was 4:1, and the EEW of the final product was 348.

TABLE 3

| | Content of materials used in Synthesis Example 3 | | | | | |
|---|---|---|---|---|---|---|
| | Ring opening process | | | Alkoxysilylation process | | |
| | Bisphenol A-based novolac epoxy (EEW = 210) | TPP | 2-allylphenol | 3-(triethoxysilyl)propyl isocyanate | N,N-diisopropyl-ethylamine | Toluene |
| Synthesis Example 3 | 25 g (0.119 mol) | 0.25 g | 3.19 g (0.024 mol) | 5.89 g (0.024 mol) | 3.08 g | 25 g |

[NMR of Final Product]
$^1$H NMR (400 MHz, DMSO): δ=7.12-6.58 (m, 20.88H), 6.01-5.79 (m, 1.03H), 5.47-5.18 (m, 1.25H), 5.13-4.80 (m, 2.76H), 4.53-4.01 (m, 10.77H), 3.86-3.58 (m, 16.04H), 3.32-3.03 (m, 4.60H), 3.01-2.90 (m, 4.00H), 2.85-2.53 (m, 10.50H), 1.56-1.26 (m, 15.01H), 1.19-1.01 (m, 11.11H), 0.59-0.46 (m, 2.05H)

[Structural Formula 3]

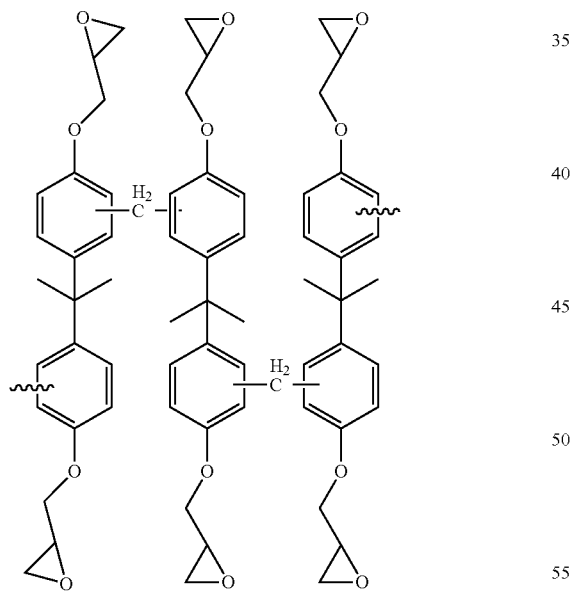

Synthesis Example 4

In Synthesis Example 4, a naphthalene-based novolac epoxy compound having an alkoxysilyl group was obtained by performing reactions in the same manner as in Synthesis Example 1 except that a naphthalene-based novolac epoxy compound of Structural Formula 4 below was used as a starting material, and the concentrations of materials were adjusted as shown in Table 4 below. The [epoxide group]:[alkoxysilyl group] mole ratio of the final product was 5:1, and the EEW of the final product was 387.

TABLE 4

Content of materials used in Synthesis Example 4

| | Ring opening process | | | Alkoxysilylation process | | |
|---|---|---|---|---|---|---|
| | Naphthalene-based novolac epoxy (EEW = 265) | TPP | Phenol | 3-(triethoxysilyl)propyl isocyanate | N,N-diisopropyl-ethylamine | Toluene |
| Synthesis Example 4 | 25 g (0.094 mol) | 0.20 g | 1.48 g (0.016 mol) | 3.89 g (0.016 mol) | 2.03 g | 25 g |

[NMR of Final Product]

$^1$H NMR (400 MHz, DMSO): δ=8.04-8.02 (m, 2.07H), 7.89-7.52 (m, 10.09H), 7.39-7.01 (m, 11.53H), 6.59-6.52 (m, 4.68H), 4.52-3.60 (m, 33.97H), 3.33-3.28 (m, 5.35H), 2.98-2.90 (m, 2.27H), 2.75-2.59 (m, 13.01H), 1.56-1.39 (m, 2.21H), 1.20-1.11 (m, 10.09H), 0.57-0.49 (m, 2.10H)

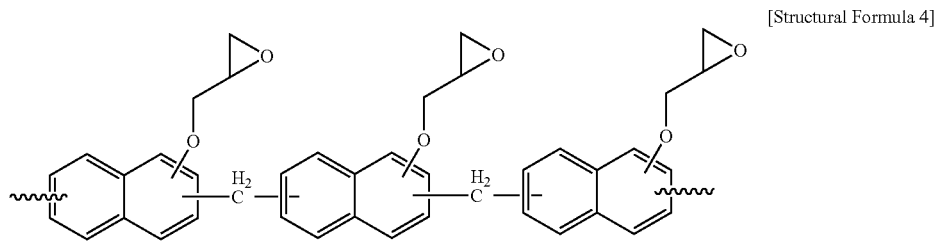

[Structural Formula 4]

Synthesis Example 5

In Synthesis Example 5, a naphthalene-based multifunctional epoxy compound having an alkoxysilyl group was obtained by performing reactions in the same manner as in Synthesis Example 1 except that a naphthalene-based multifunctional compound of Structural Formula 5 below was used as a starting material, and the concentrations of materials were adjusted as shown in Table 5 below. The [epoxide group]:[alkoxysilyl group] mole ratio of the final product was 5:1, and the EEW of the final product was 263.

TABLE 5

Content of materials used in Synthesis Example 5

| | Ring opening process | | | Alkoxysilylation process | | |
|---|---|---|---|---|---|---|
| | Naphthalene-based multifunctional epoxy (EEW = 162) | TPP | Phenol | 3-(triethoxysilyl)propyl isocyanate | N,N-diisopropyl-ethylamine | Toluene |
| Synthesis Example 5 | 25 g (0.154 mol) | 0.20 g | 2.42 g (0.026 mol) | 6.36 g (0.026 mol) | 3.32 g | 25 g |

[NMR of Final Product]

$^1$H NMR (400 MHz, DMSO): δ=7.88-6.84 (m, 14.42H), 4.84 (s, 1.94H), 4.57-3.71 (m, 8.82H), 3.31-3.15 (m, 3.77H), 2.99-2.54 (m, 10.53H), 1.57-1.37 (m, 1.60H), 1.17-1.11 (m, 7.11H), 0.56-0.51 (m, 1.50H)

[Structural Formula 5]

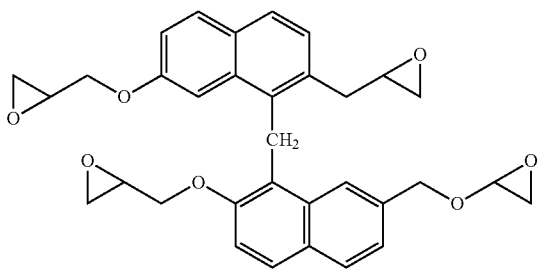

Synthesis Example 6

In Synthesis Example 6, an aminophenol epoxy compound having an alkoxysilyl group was obtained by performing reactions in the same manner as in Synthesis Example 1 except that an aminophenol epoxy compound of Structural Formula 6 below was used as a starting material, 2-allylphenol was used as a ring-opening agent, and the concentrations of materials were adjusted as shown in Table 6 below. The [epoxide group]:[alkoxysilyl group] mole ratio of the final product was 6.7:1, and the EEW of the final product was 166.

TABLE 6

| Content of materials used in Synthesis Example 6 | | | | | |
|---|---|---|---|---|---|
| Ring opening process | | | Alkoxysilylation process | | |
| Aminophenol epoxy (EEW = 100) | TPP | 2-allylphenol | 3-(triethoxysilyl)propyl isocyanate | N,N-diisopropyl-ethylamine | Toluene |
| Synthesis Example 6 — 25 g (0.250 mol) | 0.20 g | 4.36 g (0.032 mol) | 8.03 g (0.032 mol) | 4.20 g | 25 g |

[NMR of Final Product]
$^1$H NMR (400 MHz, DMSO): δ=7.25-6.75 (m, 6.05H), 6.02-5.79 (m, 0.42H), 5.47-5.17 (m, 0.44H), 5.15-4.81 (m, 0.86H), 4.22-4.02 (m, 3.69H), 3.80-3.54 (m, 4.08H), 3.36-3.25 (m, 2.61H), 3.11-3.06 (m, 1.76H), 3.01-2.90 (m, 0.82H), 2.83-2.80 (m, 0.87H), 2.74-2.71 (m, 1.78H), 2.68-2.66 (m, 0.88H), 2.57-2.54 (m, 1.77H), 1.56-1.38 (m, 0.80H), 1.17-1.12 (m, 3.87H), 0.55-0.50 (m, 0.78H)

[Structural Formula 6]

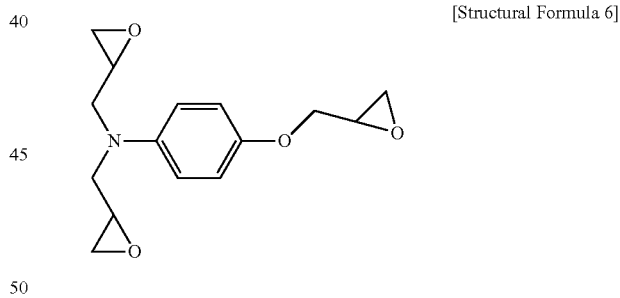

Synthesis Example 7

In Synthesis Example 7, a triphenylmethane epoxy compound having an alkoxysilyl group was obtained by performing reactions in the same manner as in Synthesis Example 1 except that a triphenylmethane epoxy compound of Structural Formula 7 below was used as a starting material, and the concentrations of materials were adjusted as shown in Table 7 below. The [epoxide group]:[alkoxysilyl group] mole ratio of the final product was 1:1, and the EEW of the final product was 662.

TABLE 7

| Content of materials used in Synthesis Example 7 | | | | | |
|---|---|---|---|---|---|
| Ring opening process | | | Alkoxysilylation process | | |
| Triphenyl methane epoxy (EEW = 160) | TPP | Phenol | 3-(triethoxysilyl)propyl isocyanate | N,N-diisopropyl-ethylamine | Toluene |
| Synthesis Example 7    25 g (0.156 mol) | 0.20 g | 1.91 g (0.078 mol) | 5.02 g (0.078 mol) | 2.62 g | 25 g |

[NMR of Final Product]
$^1$H NMR (400 MHz, DMSO): δ=7.40-7.20 (m, 0.71H), 7.02-6.73 (m, 12.58H), 5.38 (s, 0.99H), 4.50-4.09 (m, 4.76H), 3.82-3.61 (m, 4.99H), 3.40-3.30 (m, 2.61H), 3.00-2.91 (m, 0.83H), 2.92-2.87 (m, 2.63H), 2.76-2.73 (m, 2.65H), 1.57-1.38 (m, 0.81H), 1.17-1.12 (m, 3.75H), 0.56-0.48 (m, 0.76H)

[NMR of Final Product]
$^1$H NMR (400 MHz, DMSO): δ=7.40-7.20 (m, 0.78H), 7.02-6.89 (m, 0.52H), 4.22-4.09 (m, 1.50H), 4.06-3.85 (m, 4.71H), 3.78-3.61 (m, 2.61H), 3.17-3.15 (m, 2.65H), 3.01-2.90 (m, 0.54H), 2.76-2.73 (m, 2.63H), 2.62-2.58 (m, 2.66H), 1.56-1.37 (m, 0.53H), 1.17-1.12 (m, 2.51H), 0.56-0.49 (m, 0.51H)

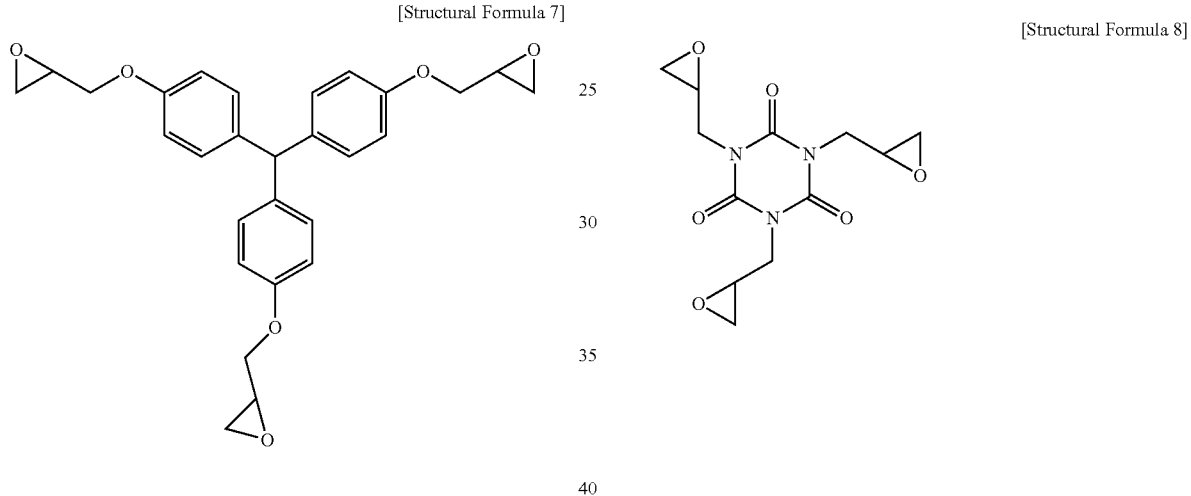

[Structural Formula 7]

[Structural Formula 8]

Synthesis Example 8

In Synthesis Example 8, an isocyanurate epoxy compound having an alkoxysilyl group was obtained by performing reactions in the same manner as in Synthesis Example 1 except that a triglycidyl isocyanurate epoxy compound of Structural Formula 8 below was used as a starting material, tricyclohexylphosphine (PCy$_3$) was used as a ring-opening agent, and the concentrations of materials were adjusted as shown in Table 8 below. The [epoxide group]:[alkoxysilyl group] mole ratio of the final product was 10:1, and the EEW of the final product was 150.

Synthesis Example 9

In Synthesis Example 9, a tetraphenylethane-based epoxy compound having an alkoxysilyl group was obtained by performing reactions in the same manner as in Synthesis Example 1 except that a tetraphenylethane-based epoxy compound of Structural Formula 9 below was used as a starting material, and the concentrations of materials were adjusted as shown in Table 9 below. The [epoxide group]:[alkoxysilyl group] mole ratio of the final product was 3.3:1, and the EEW of the final product was 377.

TABLE 8

| Content of materials used in Synthesis Example 8 | | | | | |
|---|---|---|---|---|---|
| Ring opening process | | | Alkoxysilylation process | | |
| Triglycidyl isocyanurate (EEW = 105) | PCy3 | Phenol | 3-(triethoxysilyl)propyl isocyanate | N,N-diisopropyl-ethylamine | Toluene |
| Synthesis Example 8    25 g (0.238 mol) | 0.13 g | 2.04 g (0.022 mol) | 5.35 g (0.022 mol) | 2.80 g | 25 g |

TABLE 9

| Content of materials used in Synthesis Example 9 | | | | | | |
|---|---|---|---|---|---|---|
| Ring opening process | | | Alkoxysilylation process | | | |
| Tetraphenylethane-based epoxy (EEW = 210) | TPP | Phenol | 3-(triethoxysilyl)propyl isocyanate | N,N-diisopropyl-ethylamine | Toluene | |
| Synthesis Example 9 | 25 g (0.119 mol) | 0.2 g | 2.61 g (0.028 mol) | 6.85 g (0.028 mol) | 3.58 g | 25 g |

[NMR of Final Product]
$^1$H NMR (400 MHz, DMSO): δ=7.58-6.54 (m, 19.25H), 4.50-3.55 (m, 15.75H), 3.34-3.20 (m, 2.87H), 2.99-2.58 (m, 9.59H), 1.56-1.37 (m, 1.67H), 1.16-1.06 (m, 8.51H), 0.61-0.45 (m, 1.61H)

[Structural Formula 9]

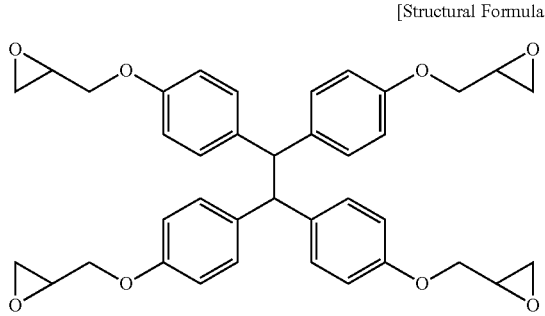

Comparative Synthesis Example 1: Comparison of Ring

Opening Reaction Processes

After a ring opening reaction was carried out under ring opening conditions of an existing preparation method (Korean Patent Registration No. 10-1655857), alkoxysilylation was performed to prepare an epoxy compound having an alkoxysilyl group. Then, Synthesis Example 1 and Comparative Synthesis Example 1 were compared with each other. The degree of ring opening was controlled to adjust the [epoxide group]: [alkoxysilyl group] mole ratio of the epoxy compound having an alkoxysilyl group to be 4:1.

25 g of a cresol novolac epoxy compound (Structural Formula 1 above, EEW 220, 0.114 mol), 0.83 g of NaOH, 1.01 of tetraethylammonium bromide (NEt$_4$Br), 50 g of tetrahydrofuran (THF), 50 g of CH$_3$CN, and 68 g (1.48 mol) of ethanol (EtOH) were added into a two-neck flask at room temperature and were stirred at 26° C. for 4 hours. Thereafter, the solvent and an excess of the ethanol were removed using a rotary evaporator, and then 5.62 g of 3-(triethoxysilyl) propyl isocyanate, 2.94 g of N,N-diisopropylethylamine (DIPEA), and 130 g of CH$_3$CN were added to the flask. Then, the flask was heated and stirred at 65° C. for 20 hours. Thereafter, the flask was cooled to room temperature, and the N,N-diisopropylethylamine and the solvent were removed using a rotary evaporator. Then, after drying using a vacuum pump, a final product was obtained.

[Necessity of Purification Process]
No alkoxysilyl functional group peak (that is, ethoxy (—OEt)) was observed in the NMR graph of the final product obtained in Comparative Synthesis Example 1 by performing a ring opening step under ring opening conditions of the related art and performing an alkoxysilylation step without a purification step such as a workup process. This is probably due to the reaction between remaining NaOH and ethoxysilane (Si—OEt). In addition, many unclear peaks were observed in NMR, and based on this, it could be confirmed that by-products were produced through additional side reactions.

As described above, in the method of the related art (Comparative Synthesis Example 1), substances such as NaOH and ammonium salts used in the ring opening step remained in the product, and thus when the alkoxysilylation reaction was performed without a purification process, (1) the epoxy compound having an alkoxysilyl group was not obtained but (2) various by-products were produced. Therefore, a purification step such as a workup process was required after a ring opening reaction performed under ring opening conditions of the related art. That is, washing using ethyl acetate and water is required, and additional drying (drying using MgSO$_4$ and solvent evaporation) are required to remove remaining moisture because the second step is affected by remaining water used in the washing.

However, in Synthesis Example 1 of the present disclosure, a strong base such as NaOH, an ammonium salt, water, and the like were not used, and thus an additional purification step was not required after a ring opening reaction. That is, after the ring opening reaction in the first process, only a solvent was removed by drying without separate purification process, and the alkoxysilylation step was performed in situ continuously to obtain the epoxy compound having an alkoxysilyl group without the formation of by-product.

[Quantitative Reaction]
In the ring opening step in Synthesis Example 1, 0.023 mol of phenol was used as a ring-opening agent to open the ring of 20 mol % (0.114 mol) of the epoxide group of the starting material. The degree of ring opening of the starting material was measured from NMR results, that is, by measuring a decrease in the H-value of the epoxide group. As shown in Table 10 below, in Synthetic Example 1, the epoxide group quantitatively reacted with the ring-opening agent, and thus a target degree of ring opening was achieved. However, in Comparative Synthesis Example 1, it was confirmed that the reactants did not react quantitatively in the ring opening process. That is, 1.48 mol of ethanol, which was 13 times the concentration (0.114 mol) of the epoxide group of the starting material was used to open the ring of 20 mol % of the epoxide functional group.

TABLE 10

Content of ring-opening agent and degree of ring opening
of epoxide group (Comparative Synthesis Example 1, NMR)

| Ringing opening of present disclosure | | Comparative Ring opening | |
|---|---|---|---|
| Concentration of ring-opening agent | Degree of ring opening (mol %) | Concentration of ring-opening agent | Degree of ring opening (mol %) |
| Phenol, 0.023 mol [Phenol]/ [Epoxide group] = 20 mol % | 20 | Ethanol, 1.48 mol [Ethanol]/ [Epoxide group] = 1300 mol % | 20 |

Comparative Synthesis Example 2

An epoxy resin having an alkoxysilyl group was synthesized according to a method of the related art by using a naphthalene-based multifunctional epoxy compound as a starting material. In a ring opening reaction, the first process, the degree of ring opening with time was first measured, and then the reaction was progressed under condition where about 30 mol % of the epoxide group was opened and finally epoxy resin having an alkoxysilyl group was synthesized.

The First Step: Ring Opening Reaction 25 g of a naphthalene-based multifunctional epoxy compound (Structural Formula 5 above, EEW 162, 0.154 mol), 8.02 g of NaOH, 9.72 g of tetraethylammonium bromide ($NEt_4Br$), 65 g of tetrahydrofuran (THF), 2.72 g of $CH_3CN$, and 177 g (3.85 mol) of ethanol (EtOH) were added into a two-neck flask at room temperature and were stirred at 26° C. for 1 hour to 24 hours. Thereafter, 30 g of an ammonium chloride ($NH_4Cl$) saturated solution was added to the flask, and the flask was stirred for 3 minutes. Then, the solvent was removed using a rotary evaporator, and workup was performed using 400 g of ethyl acetate (EA) and 300 g of water to separate an organic layer. $MgSO_4$ was added to the separated organic layer to remove remaining $H_2O$, followed by filtration and the solvent removal. In this manner, an epoxy ring-opened epoxy intermediate product was obtained.

In Comparative Synthesis Example 2, the amount of the ring-opening agent (ethanol, 3.85 mol) was 25 times higher than that of the epoxide group (0.154 mol). FIG. 1 shows the degree of ring opening (NMR measurement) of the epoxide group measured under the conditions of Comparative Synthesis Example 2 with time.

Based on the results shown in FIG. 1, a ring opening reaction was performed for about 100 minutes to open the ring of 30 mol % of the epoxide group, and then an alkoxysilylation reaction was performed in a second step as described below.

The Second Process: Alkoxysilylation Reaction 20 g of an intermediate obtained in the first process, 25.9 g of 3-(triethoxysilyl)propyl isocyanate, 13.5 g of N,N-diisopropylethylamine (DIPEA), and 500 g of $CH_3CN$ were added into a two-neck flask and were stirred at 65° C. for 20 hours. After the reaction, hexane was added to a crude product from which a solvent had been removed using a rotary evaporator, and the product was kept at −15° C. for precipitation. After removing a supernatant, a process where the hexane was added for precipitation was repeated twice to obtain a final product. The mole ratio of [epoxide group]:[alkoxysilyl group] for a synthesized epoxy compound having an alkoxysilyl group was 2.5:1.

Figure 2:
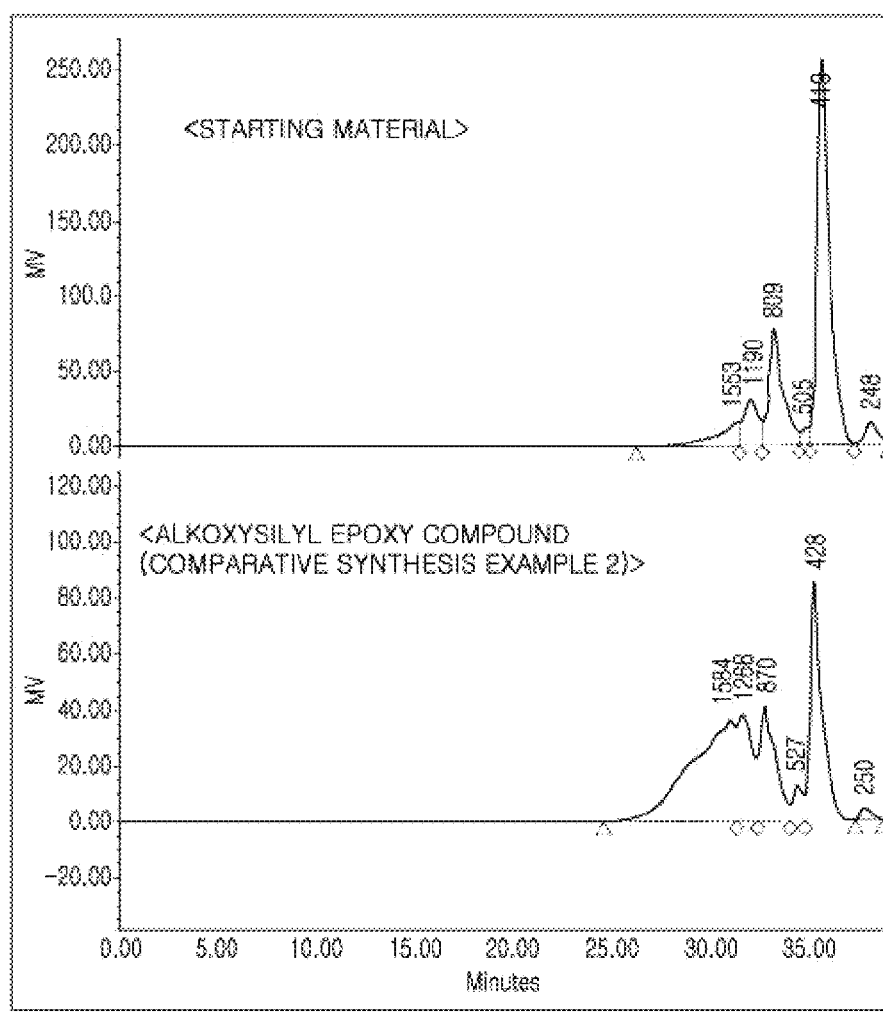
FIG. 2 is a graph (results of gel permeation chromatography (GPC)) showing variations in the molecular weight of an epoxy compound having an alkoxysilyl group prepared in Comparative Synthesis Example 2.

The molecular weight distribution of the epoxy compound of a naphthalene-based multifunctional structure having an alkoxysilyl group prepared in Comparative Synthesis Example 2 was measured using gel permeation chromatography (GPC) as shown in FIG. 2. Unlike the epoxy compound having an alkoxysilyl group prepared in Synthesis Example 5, the epoxy compound having an alkoxysilyl group prepared in Comparative Synthesis Example 2 by using NaOH showed the increased molecular weight and molecular weight distribution as shown in FIG. 2.

Comparative Synthesis Example 3

A ring opening reaction was performed in the same manner as in Synthesis Example 1 except that the ring opening reaction was performed at room temperature, and it was observed by NMR that the epoxide group of a starting material was not ring-opened.

Comparative Synthesis Example 4

A ring opening reaction of an epoxy compound was performed in the same manner as in Synthesis Example 1 except for the conditions in Table 11 below. As shown in Table 11 below, in Comparative Synthesis Example 4, a phenol novolac curing agent (Meiwa Plastic Industries, HEW=107) was used instead of phenol.

TABLE 11

Content of materials used in Comparative Synthesis Example 4

| | Inventive Example (phenol) | | | Comparative synthesis example 4 (Phenol novolac curing agent) | | |
|---|---|---|---|---|---|---|
| Formulation | Cresol novolac epoxy compound 5 g | TPP 0.05 g | Phenol 1.49 g | Cresol novolac epoxy compound 5 g | TPP 0.05 g | Phenol novolac curing agent 1.70 g |
| Reaction conditions | 110° C., 12 hours | | | | | |
| Product characteristics | Substance obtained by the reaction with phenol (corresponding to intermediate product of present disclosure) is soluble in organic solvents such as methyl ethyl ketone (MEK) and undergoes alkoxysilylation reaction in second step. | | | Substance obtained by reaction with phenol novolac curing agent is not soluble in solvent and is not melted by heat, and can thus not undergo the alkoxysilylation reaction in second step. | | |

Due to the use of the phenol novolac curing agent, an epoxy cured product having a crosslinked structure was formed by reaction between an epoxy compound and the curing agent. The epoxy cured product was not dissolved in a solvent and melted by heat, and thus an alkoxysilylation reaction could not proceed in a second step.

B. Physical Property Evaluation: Preparation of Cured Products and Heat Resistance Evaluation (1) Preparation of Epoxy Filler Composites (Cured Products)

An epoxy compound, silica (average particle size: 15 μm), and wax were dissolved in methyl ethyl ketone according to the composition of formulation illustrated in Table 12 below so that a solid content to be 70 wt %. This mixture solution was stirred for 20 minutes, and after adding a curing agent thereto, the mixture solution was further stirred for 10 minutes. Then, a catalyst was added to the mixture solution, and the mixture solution was stirred for 10 minutes to make the mixture solution uniform. Then, the mixture solution was inserted into a convection oven heated to 80° C. to remove the solvent, and was cured at 120° C. for 2 hours, at 180° C. for 2 hours, and at >200° C. for 2 hours by using a preheated hot press. In this manner, epoxy filler (inorganic particles) composites (5 mm×5 mm×3 mm) were obtained.

(2) Heat Resistance Evaluation

Figure 3:
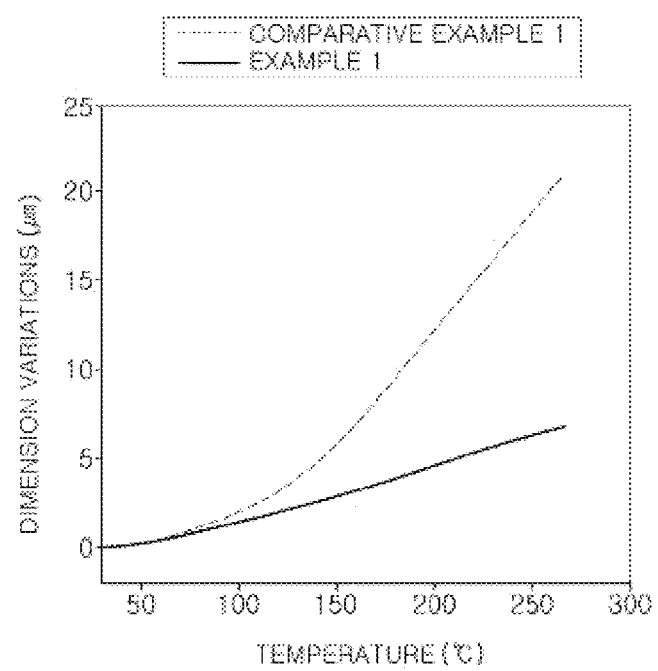
FIG. 3 is a graph to show thermal expansion characteristics of epoxy composites of Example 1 and Comparative Example 1.

Dimensional variations of cured products having composition of formulation as shown in Table 12 below were evaluated with respect to temperature by using a thermomechanical analyzer, and results thereof are shown in Table 12 below. In addition, FIG. 3 is a graph showing dimensional variations of cured composites obtained in Example 1 and Comparative Example 1 with respect to temperature. Epoxy filler composite samples had a size of 5×5×3 (mm³).

TABLE 12

Heat resistance of filler composites

| | Compound (synthesis example No.) | | *E1 | E2 | E3 | E4 | E5 | E6 | E7 | E8 | E9 | **CE1 | CE2 |
|---|---|---|---|---|---|---|---|---|---|---|---|---|---|
| Composition of formulation (g) | Epoxy compound | ***SE1 | 3.00 | | | | | | | | | | 3.00 |
| | | SE2 | | 3.00 | | | | | | | | | |
| | | SE3 | | | 3.00 | | | | | | | | |
| | | SE4 | | | | 3.00 | | | | | | | |
| | | SE5 | | | | | 3.00 | | | | | | |
| | | SE6 | | | | | | 3.00 | | | | | |
| | | SE7 | | | | | | | 3.00 | | | | |
| | | SE8 | | | | | | | | 3.00 | | | |
| | | SE9 | | | | | | | | | 3.00 | | |
| | | YDCN[1] | | | | | | | | | | 3.00 | |
| | HF-1M[2] | | 1.07 | 0.91 | 1.11 | 1.00 | 1.46 | 2.32 | 0.58 | 2.57 | 1.02 | 1.46 | |
| | Phenol | | | | | | | | | | | | 1.28 |
| | 2P4MHZ[3] | | 0.21 | 0.21 | 0.21 | 0.21 | 0.21 | 0.21 | 0.21 | 0.21 | 0.21 | 0.21 | 0.21 |
| | WAX-E[4] | | 0.01 | 0.01 | 0.01 | 0.01 | 0.01 | 0.01 | 0.01 | 0.01 | 0.01 | 0.01 | 0.01 |
| | Silica | | 24.31 | 23.40 | 24.54 | 23.91 | 26.52 | 31.39 | 21.53 | 32.81 | 24.03 | 26.52 | 25.50 |
| Heat resistance | CTE (ppm/° C.) | $\alpha_1$ ($T < T_g$) | 7.9 | 9.2 | 8.6 | 9.7 | 9.0 | 8.8 | 8.7 | 10.3 | 9.1 | 15.8 | Not measurable |
| | | $\alpha_2$ ($T > T_g$) | 11.2 | 21.3 | 17.7 | 20.0 | 18.1 | 19.7 | 17.8 | 22.4 | 20.6 | 40.1 | |

*E: Example,
**CE: Comparative Example,
***SE: Synthesis Example
Notes)
the following compounds are used in Table 11 above
[1]Cresol novolac-based epoxy compound (YDCN-500-80P, EEW = 220 g/Eq, Kukdo Chemical Co,. Ltd.)
[2]HF-1M: phenol novolac-based curing agent (Meiwa Plastic Industries, HEW = 107)
[3]2P4MHZ: imidazole-based catalyst (Curezol, Shikoku)
[4]WAX-E: Licowax E (Clariant)

The composites of Examples 1 to 9, which were made from epoxy compounds having an alkoxysilyl group and prepared by the method of the present disclosure, showed very good thermal expansion characteristics (i.e., low coefficient of thermal expansion (CTE)) as shown in Table 12 above. As shown in FIG. 3 and Table 12, the composites of Examples 1 to 9, which were made from epoxy compounds having an alkoxysilyl group prepared by the method of the present disclosure, had very good thermal expansion characteristics compared to the composite of Comparative Example 1 which was made from an existing epoxy compound having the same core structure.

(3) Evaluation of the Possibility of Using Phenol as a Curing Agent.

Figure 4A:
FIG. 4A shows the shape and solubility of a cured molding sample prepared with the formulation of Example 1.
Figure 4B:
FIG. 4B shows the shape and solubility of a cured molding sample prepared with the formulation of Comparative Example 2.

Epoxy compounds according to the formulations of Example 1 and Comparative Example 2 were processed as molds, which were photographed as shown in FIGS. 4A and 4B, respectively. As shown in FIGS. 4A and 4B, the molded sample prepared with the formulation of Example 1 using a phenol novolac curing agent maintained its shape after the processing and was not dissolved in a solvent. Thus, Example 1 is applicable to manufacture of epoxy parts such as a semiconductor package.

However, the molded sample prepared with the formulation of Comparative Example 2 using phenol was soft and easily deformed while being taken out from a mold. In addition, the molded sample was soluble in an organic solvent (DMAc). Thus, it was confirmed that phenol did not function as a curing agent for an epoxy compound.

According to the preparation method for an epoxy compound having an alkoxysilyl group of the present disclosure, side reactions do not occur in the ring opening step unlike in preparation methods of the related art, and since a strong base which can give an influence on the alkoxysilylation reaction in the second step is not used, in situ alkoxysilylation reaction can be done without an purification (workup) step. Therefore, preparation step may be simplified, and the production of by-products may be suppressed. In addition, according to the present disclosure, the aromatic alcohol as the ring-opening agent react stoichiometrically with the epoxy compound, and thus the degree of ring opening of an epoxide group may be easily controlled by the concentration of the aromatic alcohol ring-opening agent used.

While exemplary embodiments have been shown and described above, it will be apparent to those skilled in the art that modifications and variations could be made without departing from the scope of the present invention as defined by the appended claims.

What is claimed is:

1. A method for preparing an epoxy resin having an alkoxysilyl group, the method comprising:
   performing a ring opening step by reacting at least one epoxy resin selected from a group consisting of Formulae BS, CS, FS, and IS having three or more epoxide groups with an aromatic alcohol having one hydroxyl group as a ring-opening agent in the presence of a phosphine-based catalyst and an optional solvent to provide an intermediate having a ring-opened epoxide group; and
   performing an alkoxysilylation step by reacting the intermediate having a ring-opened epoxide group with isocyanate alkoxysilane represented by Formula B below,
   wherein the phosphine-based catalyst is represented by Formula A:

PRxRyRz        Formula A in Formula A, Rx, Ry, and Rz are each independently a C1-C10 alkyl group, a C6 or C10 aryl group, or a C6-C10 cycloalkyl group,
   wherein the epoxy compound having the alkoxysilyl group following the alkoxysilylation step is represented by at least one selected from a group consisting of Formulae BF, CF, FF, and IF:

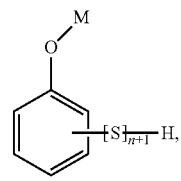

BF

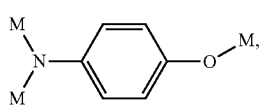

FF

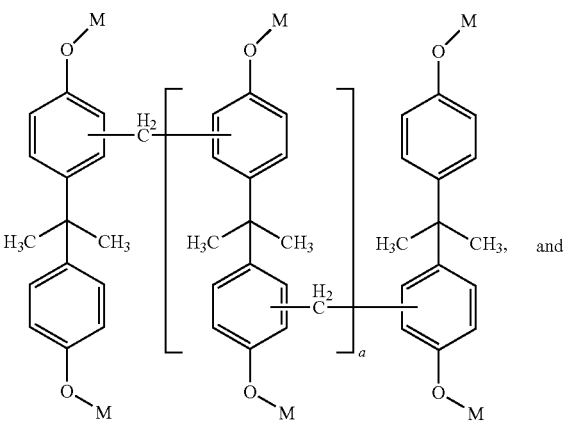

CF

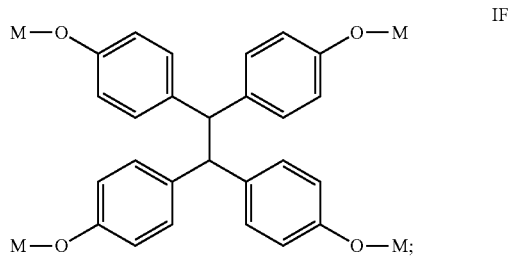

and

IF wherein in Formula BF:
S is

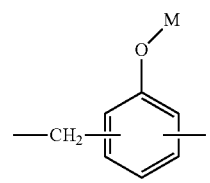

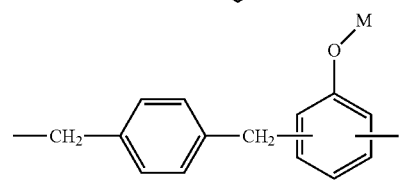

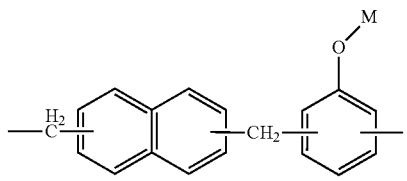

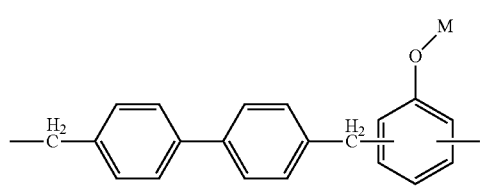

-continued

![Structures with M groups on bicyclic and biphenyl systems]

wherein in Formulae BF, CF, FF, and IF:
at least one of the M's is of Formula C;
at least two of the M's is an epoxy group of Formula E1; and remainder of M's are hydrogen, Formula E1

$$\underset{O}{\triangle}\!\!-\!CH_2\!-\!,\quad (E1)$$

Formula C $$-\!\!\underset{H}{\overset{H_2}{C}}\!-\!\underset{|}{\overset{}{C}}\!-\!\underset{}{\overset{H_2}{C}}\!-\!Y$$
with CONH—(CH$_2$)$_3$-SiR$_1$R$_2$R$_3$ on the central carbon, and,
in Formula C, at least one of R$_1$ to R$_3$ is a C1-C5 alkoxy group, and the others are C1-C10 alkyl groups, and Y is represented by Formula 3 or 4, ![Formula 3: phenoxy with Xn' substituents] (3)

or

![Formula 4: methoxy naphthyl with Xn' substituents] (4)

wherein in Formula 3 or Formula 4,
each X is independently selected from the group consisting of H, a C1 to C10 alkyl group, an allyl group, and a C6 or C10 aryl group, wherein the C6 or C10 aryl group is substitutable with a C1-C3 alkyl group, and n' is an integer from 1 to 5; and
n in Formulae BF and CF is an integer from 1 to 30,
wherein the Formulae BF, CF, FF, and IF are prepared from epoxy resins BS, CS, FS, and IS, respectively,

BS

![Structure BS: phenol with O-K and S chain]

FS

![Structure FS: aniline with N(K)$_2$ and O-K]

CS

![Structure CS: bisphenol A oligomer with O-K groups]

IS

![Structure IS: tetraphenylethane with four O-K groups]

wherein in Formulae BS, CS, FS, and IS, at least three of the K's is an epoxy group of Formula E1, and the remaining are hydrogen,
S in Formula BS is the same as in Formula BF except M in Formula BF is K as defined in Formula BS, and
n in Formulae BF and CF is the same as in Formula BS and CS, respectively, OCN(CH$_2$)$_3$SiR$_1$R$_2$R$_3$         [Formula B]

where at least one of R$_1$ to R$_3$ is a C1-05 alkoxy group, and the others are C1-C10 alkyl groups.

2. The method of claim 1, wherein in situ the alkoxysilylation step is carried out continuously following the ring opening.

3. The method of claim 1, wherein the ring opening step does not require the subsequent purification process for the intermediate product having a ring-opened epoxide group.

4. The method of claim 1, wherein the aromatic alcohol is represented by Formulae 1 or 2 below:

![Formula 1: phenol with Xn' substituents] (1)

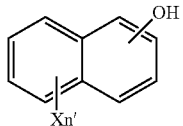
(2)

wherein in Formulae 1 and 2, each X is independently H, a C1 to C10 alkyl group, an allyl group, or a C6 or C10 aryl group, wherein the C6 or C10 aryl group is substitutable with a C1-C3 alkyl group, and n' is an integer ranging from 1 to 5.

5. The method of claim 1, wherein 0.1 to 2 parts by weight of the phosphine-based catalyst are used per 100 parts by weight of the epoxy resin having three or more epoxide groups.

6. The method of claim 1, wherein the ring opening step is performed for 10 minutes to 48 hours.

7. The method of claim 1, wherein a degree of ring opening does not need to be controlled by reaction time in the ring opening step.

8. An article comprising the epoxy resin having an alkoxysilyl group of claim 1, the article selected from an electronic material, semiconductor substrate, IC substrate, laminate in which a metal layer is provided on a base layer, prepreg, encapsulant, printed circuit board, electronic component, adhesive, painting, or composite material.

9. The method of claim 1, wherein 0.05 to 0.9 equivalents of the aromatic alcohol ring-opening agent is used per one equivalent of epoxy group of the epoxy resins selected from a group consisting of Formulae BS, CS, FS, and IS.

10. The method of claim 1, wherein the ring-opening step is performed at a temperature of 60° C. to 200° C.

* * * * *